United States Patent
Sokatch et al.

(10) Patent No.: US 6,168,945 B1
(45) Date of Patent: *Jan. 2, 2001

(54) GENES ENCODING OPERON AND PROMOTER FOR BRANCHED CHAIN KETO ACID DEHYDROGENASE OF PSEUDOMONAS PUTIDA AND METHODS

(75) Inventors: John R. Sokatch, Oklahoma City, OK (US); Pamela J. Sykes, Adelaide (AU); K. T. Madhusudhan, Oklahoma City, OK (US); Soo-Kyung Oh, deceased, late of Palo Alto, CA (US), by Ji Chang You, legal representative

(73) Assignee: The Board of Regents of the University of Oklahoma, Norman, OK (US)

( * ) Notice: Under 35 U.S.C. 154(b), the term of this patent shall be extended for 0 days.

This patent is subject to a terminal disclaimer.

(21) Appl. No.: 08/404,381

(22) Filed: Mar. 14, 1995

Related U.S. Application Data

(63) Continuation of application No. 07/603,781, filed on Oct. 19, 1990, now abandoned, which is a continuation-in-part of application No. 07/498,458, filed on Mar. 21, 1990, now abandoned, which is a continuation of application No. 07/172,148, filed on Mar. 23, 1988, now abandoned.

(51) Int. Cl.$^7$ ............................ C12N 15/52; C12N 15/31; C12N 15/67; C12N 1/21
(52) U.S. Cl. ..................... 435/252.3; 435/320.1; 435/252.33; 435/252.34; 536/24.1; 536/23.2; 536/23.7
(58) Field of Search .................. 435/252.3, 252.33, 435/320.1, 252.34; 536/23.7, 23.2, 24.1

(56) References Cited

U.S. PATENT DOCUMENTS 5,656,483 * 8/1997 Sokatch et al. .................. 536/23.2

OTHER PUBLICATIONS

Sykes et al., Apr. 1985, Journal Of Bacteriology, vol. 162, pp. 203–208, Conjugative Mapping Of Pyruvate, 2–Ketoglutarate, and Branched–Chain Keto Acid Dehydrogenase Genes in *Pseudomonas putida* Mutants.

Luthi et al., 1986, Journal of general Microbiology, vol. 132, pp. 2667–2675, The arcABC Operon Required for Fermentative Growth of *Pseudomonas aeruginosa* on Arginine: Tn5–751–assisted Cloning and Localization of Structural Genes.

Inouye et al., Jun. 1986, Journal of Bacteriology, vol. 166, pp. 739–745, Nucleotide Sequence of a DNA Segment Promoting Transcription in *Pseudomonas putida*.

Minton et al., Dec. 1983, Journal of Bacteriology, vol. 156, pp. 1222–1227, Molecular Cloning of the Pseudomonas Carboxypeptidase $G_2$ Gene and Its Expression in *Escherichia coli* and *Pseudomonas putida*.

Schell, Feb. 1983, Journal of Bacteriology, vol. 153, pp. 822–829, Cloning and Expression in *Escherichia coli* of the Naphthalene Degradation Genes from Plasmid NAH7.

Madhusudhan et al., Oct. 1990, Journal of Bacteriology, vol. 172, pp. 5655–5663, Transcriptional Analysis of the Promoter region of the *Pseudomonas putida* Branched–Chain Keto Acid Dehydrogenase Operon.

Sokatch et al., Nov. 1981, Journal of Bacteriology, vol. 148, pp. 639–646, Isolation of a Specific Lipoamide Dehydrogenase for a Branched–Chain Keto Acid Dehydrogenase from *Pseudomonas putida*.

Burns et al., Feb. 1988, Eur. Journal of Biochemistry, vol. 176, pp. 165–169, Comparison of the amino acid sequences of the transacylase components of branched chain oxoacid dehydrogenase of *Pseudomonas putida* and the pyruvate and 2–oxoglutarate dehydrogenases of *Escherichia coli*.

Sykes et al., Apr. 1987, Journal of Bacteriology, vol. 169, pp. 1619–1625, Molecular Cloning of Genes Encoding Branched–Chain Keto Acid Dehydrogenase of *Pseudomonas putida*.

Burns et al., Feb. 1988, Eur. Journal of Biochemistry, vol. 176, pp. 165–169, Comparison of the amino acid sequences of the transacylase components of branched chain oxoacid dehydrogenase of *Pseudomonas putida* and the pyruvate and 2–oxoglutarate dehydrogenases of *Escherichia coli*.

Yanisch–Perroc et al., 1985, Gene, vol. 33, pp. 103–119, Improved M13 phage cloning vectors and host strains: nucleotide sequences of the M13mp18 and $_p$UC19 vectors.

Sokatch et al., Nov. 1981, Journal of Bacteriology, vol. 148, pp. 647–652, Purification of a Branched–Chain Keto Acid Dehydrogenase from *Pseodomonas putida*.

Bahdasarian et al., 1981, Gene, vol. 16, pp. 237–247, Specific–purpose plasmid cloning vectors.

* cited by examiner

Primary Examiner—Mary E. Mosher
(74) Attorney, Agent, or Firm—Dunlap, Codding & Rogers, P.C.

(57) ABSTRACT

DNA sequences coding for branched chain keto dehydrogenase, a promoter and branched chain keto dehydrogenase, and the promoter are disclosed. Also disclosed are recombinant vectors comprising one of the foregoing DNA sequences, transformed hosts comprising one of the foregoing recombinant vectors, and a method of making the polypeptide encoded by the DNA sequence.

11 Claims, 4 Drawing Sheets

GENES ENCODING OPERON AND PROMOTER FOR BRANCHED CHAIN KETO ACID DEHYDROGENASE OF *PSEUDOMONAS PUTIDA* AND METHODS

CROSS REFERENCE TO RELATED APPLICATIONS

This application is a continuation of U.S. Ser. No. 07/603,781, filed Oct. 19, 1990, entitled GENES ENCODING OPERON AND PROMOTOR FOR BRANCHED CHAIN KETO ACID DEHYDROGENASE OF *PSEUDOMONAS PUTIDA* AND METHODS, now abandoned, which is a continuation in part application of U.S. Ser. No. 07/498,458 filed Mar. 21, 1990 entitled MOLECULAR CLONING OF GENES ENCODING BRANCHED CHAIN KETO ACID DEHYDROGENASE OF *PSEUDOMONAS PUTIDA*, now abandoned, which is a continuation of U.S. Ser. No. 07/172,148 filed Mar. 23, 1988 of the same title, now abandoned.

GOVERNMENT SUPPORT

This invention was made with government support under Public Health Service grants AM21737 and GM30428 from the National Institutes of Health. The government has certain rights in this invention.

FIELD OF THE INVENTION

The present invention relates to DNA coding for branched chain keto dehydrogenase operon and promoter, and methods of use.

SUMMARY OF THE INVENTION

The present invention comprises an isolated double stranded DNA sequence encoding a polypeptide possessing activity of branched chain keto acid dehydrogenase, and the polypeptide encoded by this sequence. The activity of the branched chain keto acid dehydrogenase is to catalyze the oxidation of branched chain keto acids. Also, the present invention comprises an isolated double stranded DNA sequence useful as a promoter of gene expression in the genus Pseudomonas or Escherichia.

The present invention further comprises a bacterium from the genus Escherichia comprising at least one recombinant vector comprising a gene encoding branched chain keto acid dehydrogenase, and a bacterium from the genus Pseudomonas comprising at least one recombinant vector comprising a promoter of gene expression having the characteristics of the DNA sequence of ATCC 88403.

The present invention further comprises a recombinant expression vector comprising a DNA sequence encoding branched chain keto acid dehydrogenase. The vector is capable of expressing branched chain keto acid dehydrogenase in a transformed microorganism or cell culture. Another recombinant expression vector comprises the DNA sequence of a promoter of gene expression in the genus Pseudomonas or Escherichia having the characteristics of the DNA sequence of ATCC 88403.

Additionally, the present invention comprises a method of producing the polypeptide branched chain keto acid dehydrogenase comprising isolating the gene encoding branched chain keto acid dehydrogenase. The isolated gene is disposed in a vector capable of permitting expression of the gene. The recombinant vector is then disposed in a host capable of permitting expression of the gene and the gene expressed.

DESCRIPTION OF THE PREFERRED EMBODIMENTS

Figure 1:
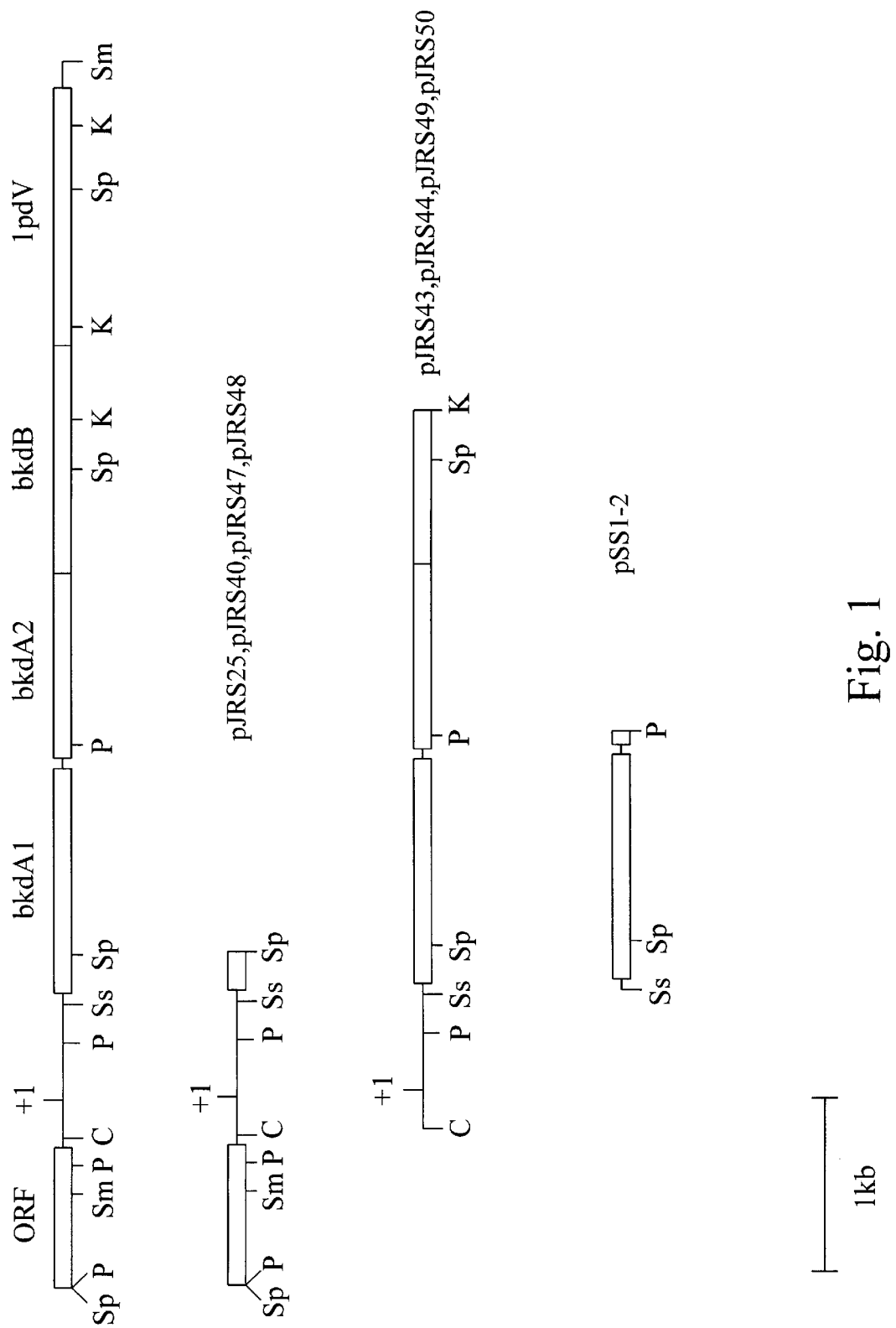
FIG. 1 shows a restriction map of the bkd operon (Sequence ID No. 1) and clones. The location of the transcriptional start of the operona is +1. The structural genes are bkdA1=E1α (Sequence ID No. 2), bkdA2=E1β (Sequence ID No. 3), bkdB=E2 (Sequence ID No. 4), and lpdV=LPD-val (Sequence ID No. 5). ORF indicates the unidentified open reading frame on the strand opposite that encoding the bkd operon (Sequence ID No. 1). Abbreviations for the restriction enzyme sites are: C=ClaI; K=KpnI; P=PstI; sp=SphI; Ss=SstI; Sm=SmaI.

Branched chain keto acid dehydrogenase is a multienzyme complex which catalyzes the oxidation of branched chain keto acids formed by the transamination of branched chain amino acids. This enzyme is induced in *Pseudomonas putida* and *Pseudomonas aeruginosa* by growth in media containing branched chain amino acids or branched chain keto acids, the latter being the true inducers. Branched chain keto acid dehydrogenase purified from *P. putida* or *P. aeruginosa* consists of three functional components, E1 (Sequence ID No. 2 and Sequence ID No. 3), E2 (Sequence ID No. 4), and E3 (Sequence ID No. 5).

The E1 component (Sequence ID No. 2 and Sequence ID No. 3) consists of two nonidentical subunits, E1α (Sequence No. 2) and E1α (Sequence ID No. 3), and catalyzes the oxidative decarboxylation of the keto acid substrates. The E2 component (Sequence ID No. 4) contains covalently bound lipoic acid which is reduced by E1 and to which the acyl agroup becomes attached. The E3 component (Sequence ID No. 5) of Pseudomonas branched chain keto acid dehyrogenase is a specific lipoamide dehydrogenase named LPD-val since it is induced in media containing valine or other branched chain amino acids.

The present invention comprises the gene that encodes for branched chain keto acid dehydrogenase (hereafter "bkad gene") produced by recombinant DNA techniques. By using the recombinant bkad gene, branched chain keto acid dehydrogenase can now be economically produced.

The present invention also comprises the bkad gene and any promoter which expresses the gene of the present invention. One example of a promoter of the present invention is the promoter normally found in *Pseudomonas putida* which expresses the bkad gene (herafter "bkad promoter"). The bkad promoter (Sequence ID No. 6) may also be used to express homologous and heterologous genes in Pseudomonas for genes other than bkad genes.

The genus Pseudomonas can be a better host for use in recombinant DNA techniques than the genus Escherichia. Many genes expressed in *E. coli*, the usual host used for recombinant DNA procedures, produce proteins that are insoluble and improperly folded. In order to retrieve the protein of interest, the protein must be dissolved in denaturing agents and slowly allowed to refold. Rarely does the protein fold in the proper configuration due to the presence of granules, therefore, the advantage of over-expression is lost. In a preferred embodiment, genes expressed from the bkad promoter (Sequence ID No. 6) expressed in *Pseudomonas putida* at least ten-fold greater than when expressed from the β-lactamase promoter of pKT230 and 50–100 fold greater than in the wild type organism of *Pseudomonas putida*.

The gene of interest could be inserted immediately behind the bkad promoter (Sequence ID No. 6) and leader of the present invention which would control the expression of this gene. The resulting plasmid would then be transferred to a Pseudomonas host such as *Pseudomonas putida* grown in a simple medium such as L-broth, which would result in high expression of the gene of interest without forming granules.

Some examples of recombinant plasmids constructed in accordance with the present invention are pJRS54, pJRS55 and pSS1-1. pJRS54 comprises an insert of *Pseudomonas putida* genomic DNA comprising the promoter, leader, ribosome binding site and the four structural genes of the branched chain keto acid dehydrogenase operon. The vector is pUC19 and the host is *Escherichia coli* DH5α. pJRS54 has been deposited in the American Type Culture Collection at Rockville, Md. under number ATCC 68405.

pJRS55 comprises the promoter, leader, ribosome binding site and the coding sequence of the four N-terminal amino acids of the first protein encoded by the branched chain keto acid dehydrogenase operon. The vector is pKT240 and the host is *Escherichia coli* DH5α. pJRS55 has been deposited in the American Type Culture Collection at Rockville, Md. under number ATCC 68403.

pSS1-1 comprises the ribosome binding site and the four structural genes of the branched chain keto acid dehydrogenase operon. The vector is pKT230 and the host is Pseudomonas putida JS112. pSS1-1 has been deposited in the American Type Culture Collection at Rockville, Md. under number ATCC 68404. This plasmid may be used when a promoter other than the bkad promoter is to be used.

Branched chain keto acid dehydrogenase produced by the bkad gene of the present invention may be used to increase the yield of an end-product of a metabolic pathway by increasing the flow of precursors. For example, the avermectin group of antibiotics produced by *Streptomyces avermitilis* contain branched chain fatty acids that are formed by the action of branched chain keto acid dehydrogenase. The commerical preparation of the avermectin antibiotics can be increased by providing a sufficient amount of branched chain keto acid dehydrogenase. In a preferred embodiment, *Steptomyces avermitilis* can be transformed with pJRS54 in a multi-copy Steptomyces vector.

The following examples illustrate the practice of preferred embodiments of the present invention. However, the present invention is not limited to the examples set forth.

EXAMPLE 1

Materials and Methods

Bacterial Strains, Plasmids, Phage and Culture Conditions
The strains, plasmids and phage used are as follows:

TABLE 1

| Strain, plasmid, or phage | Relevant genotype or phenotype[a] | Source or reference |
|---|---|---|
| *P. putida* | | |
| PpG2 | Wild type | I. C. Gunsalus |
| JS113 | bkdA1 (Sequence ID No. 2) bkdA2 (Sequence ID No. 3) | Sykes, P. J., et al., "Conjugative mapping of pyruvate, 2-ketoglutarate and branched chain keto acid dehydrogenase genes in *Pseudomonas putida* mutants." J.Bacteriol. 162:203–208 (1985) |
| KT2440 | mt-2 hsdR1 (r⁻ m⁺) | Köhler, T., et al., "Involvement of *Pseudomonasputida* RpoN sigma factor in regulation of various metabolic functions." J. Bacteriol. 171:4326–4333 (1989) |
| rpoN mutant | Km[r] rpoN⁻ | Köhler, T., et al., "Involvement of *Pseudomonasputida* RpoN sigma factor in regulation of various metabolic functions." J. Bacteriol. 171:4326–4333 (1989) |
| *E. coli* | | |
| TB1 | ara lacZ δM15 δ(lac⁻proAB) φ80 hsdR17 (r⁻ m⁺) strA | BRL |
| DH5α | F⁻φ80d lacZ δM15 δ(lacZYA-argF) U169 endA1 hsdR17 (r⁻ m⁺) recA1 supE44 lambda- thi-1 gyrA relA1 | BRL |
| JM101 | δ(lac-proAB) supE thi [F', traD36, proAB, lacI<sup>q</sup>Z δM15] | Yanisch-Perron, C., et al., "Improved M13 phage cloning vectors and host strains: nucleotide sequences of the M13mp18 and pUC19 vectors." Gene. 33:103–119 (1985) |
| Plasmids | | |
| pKT240 | IncQ mob⁺ Ap[r] Km[r] | Bagdasarian, M. M., et al., "Activity of the hybrid trp-lac (tac) promoter of *Escherichia coli* in *Pseudomonas putida*. Construction of broad-host-range, controlled-expression vectors." Gene. 26:273–282 (1983) |
| pJRS25 | bkd promoter (Sequence ID No. 6) in pUC19, same orientation as lacZ | described herein |
| pJRS40 | bkd promoter (Sequence ID No. 6) in pUC19, opposite to lacZ | described herein |
| pJRS43 | bkd promoter (Sequence ID No. 6) with bkdA1 (Sequence ID No. 2) and bkdA2 (Sequence ID No. 3) in pUC19, opposite to lacZ | described herein |
| pJRS44 | bkd promoter (Sequence ID No. 6) with bkdA in pUC19, same |  described herein |

TABLE 1-continued

| Strain, plasmid, or phage | Relevant genotype or phenotype[a] | Source or reference |
|---|---|---|
| pJRS47 | as orientation as lacZ Same insert as pJRS25 and pJRS40 in pKT240, opposite to aph | described herein |
| pJRS48 | Same insert as JRS25 and pJRS40 in pKT240, same orientation as aph | described herein |
| pJRS49 | Same insert as pJRS43 and pJRS44 in pKT240, opposite to aph | described herein |
| pJRS50 | Same insert as pJRS43 and pJRS44 in pKT240, same orientation as aph | described herein |
| pRK2013 | ColE1 mob[+] tra[+] (RK2)Km[r] | Goldberg, J. B., et al., "Cloning and expression in *Pseudomonas aeruginosa* of a gene involved in the production of alginate." J. Bacteriol. 158:1115–1121 (1984) |
| pUC19 | Ap[r] | Yanisch-Perron, C., et al., "Improved M13 phage cloning vectors and host strains: nucleotide sequences of the M13mp18 and pUC19 vectors." Gene. 33:103–119 (1985) |
| Phage | | |
| M13mp19 | | Yanisch-Perron, C., et al., "Improved M13 phage cloning vectors and host strains: nucleotide sequences of the M13mp18 and pUC19 vectors." Gene. 33:103–119 (1985) |

[a]Gene designations for *P. putida* are: bkdA1, E1α subunit and bkdA2, E1β subunit of branched chain keto acid dehydrogenase.

The growth conditions and media used are described in Sykes, P. U. et al., "Molecular cloning of genes encoding branched chain keto acid dehydrogenase of *Psudomonas putida*", J. Bacteriol. 169: 1619–1625 (1987) and Sykes, P. J., et al., "Conjugative mapping of pyruvate, 2-ketoglutarate and branched chain keto acid dehydrogenase genes in *Pseudomonas putida* mutants", J. Bacteriol. 162:203–208 (1985). Pseudomonas isolation agar was from DIFCO Laboratories.

RNA was prepared from *P. putida* grown in a minimal medium with either 0.3% valine and 0.1% isoleucine (valine/isoleucine medium) according to the method described in Sykes, P. J., et al., "Conjugative mapping of pyruvate, 2-ketoglutarate and branched chain keto acid dehydrogenase genes in Pseudomonas putida mutants", J. Bacteriol. 162:203–208 (1985), or 10 mM glucose as the sole carbon source or in L-broth according to Lennox, E. S., "Transduction of linked genetic characters of the host by bacteriophage P1", Virol. 1:190–205 (1955).

GASV medium was used for mutants affected in keto acid dehydrogenases, including branched chain keto acid dehydrogenase and contains 10 mM glucose, 2 mM acetate, 2 mM succinate, 0.3% L-valine and 0.1% L-isoleucine according to the method described in Sykes, P. J. et al., "Molecular cloning of genes encoding branched chain keto acid dehydrogenase of *Pseudomonas putida*", J. Bacteriol. 169: 1619–1625 (1987). When antibiotic supplements were added, the final concentrations were (µg/ml): ampicillin, 200; kanamycin, 90; and carbenicillin, 2000.

Enzymes and Chemicals

Restriction endonucleases and other DNA enzymes were obtained from Promega Corporation or Bethesada Research Laboratories, Inc. The (τ-$^{32}$P)dCTP, (α-$^{32}$P)dATP were from New England Nuclear Corporation. Isopropyl-β-D-thiogalactopryanoside (IPTG), 5-bromo-4-chloro-3-indolyl-β-D-galactopyranoside (X-gal), RNase A, ampicillin, kanamycin and carbenicllin were from Sigma Chemical Co. All other chemicals were of analytical reagent grade.

Enzyme Assays

The assay for E1 component (Sequence ID No. 2 and Sequence ID No. 3) of branched chain keto acid dehydrogenase was performed in the presence of excess E2 (Sequence ID No. 4) and LPD-val (Sequence ID No. 5). The latter two components were proved by a 90,000×g supernatant fraction of *E. coli* TB1 (pKRS3) according to the method described in Sykes, P. U. et al, "Molecular cloning of genes encoding branched chain keto acid dehydrogenase of *Pseudomonas putida*", J. Bacteriol. 169: 1619–1625 (1987).

The conditions of the assay for branched chain keto acid dehydrogenase are described in Sokatch, J. R. et al., "Purification of a branched chain keto acid dehydrogenase for *Pseudomonas putida*", J. Bacteriol. 148: 647–652 (1981). The assay for E1 (Sequence ID No. 2 and Sequence ID No. 3) activity used the same conditions except that the assay was supplemented with 300 µg of a 90,000×g supernatant fraction prepared from *E. coli* TB1 (pJRS3). This fraction supplies excess E2 (Sequence ID No. 5) and LPD-val (Sequence ID No. 5) so that the rate of NADH formation depends on amount of E1α (Sequence ID No. 2) and E1β (Sequence ID No. 3).

Nucleic Acid Preparations

Plasmid and phage DNA were prepared according to the method of Maniatis, T, et al., *Molecular cloning: A Laboratory Manual*, 1987, Cold Spring Harbor Laboratory, Cold Spring Harbor, N. Y. RNA was prepared according to the method of Burns, G., et al., "Sequence analysis of the lpdV gene for lipoamide dehydrogenase of branched chain oxoacid dehydrogenase of *Pseudomonas putida*", Eur. J. Biochem. 179:61–69. Nick translation of DNA was performed according to manufacturer's recommendations using a kit from Bethesda Research Laboratories. End labelling of synthetic oligonucleotides was performed according to the method of Maniatis, T, et al., *Molecular cloning: A Laboratory Manual*, 1987, Cold Spring Harbor Laboratory, Cold Spring Harbor, N.Y.

Screening of *P. putida* Genomic Library

An SphI genomic library of *P. putida* DNA in pUC19 in *E. coli* TB1 was used. The nick translated probe for screening the library was prepared from pSS1-2 [see Burns, G., et al., "Similarity of the E1 subunits of branched chain-oxoacid dehydrogenase from *Pseudomonas putida* to the corresponding subunits of mammalian branched chain-oxoacid and pyruvate dehydrogenases", Eur. J. Biochem. 176:311–317 (1988)] by digestion with Sst I and PstI.

This relased a 1.45 kb fragment of DNA that included bkdA1 (Sequence ID No. 2) and part of bkdA2 (Sequence ID No. 3). The library was plated on L-agar containing ampicillin and the colonies were lifted using Colony-Plaque screen (NEN Corporation). DNA fixation, hybridization and washing conditions were those suggested by the manufacturer.

Subcloning and DNA Sequencing

The genomic DNA insert from the positive clone, pJRS25, was excised from pUC19 by digesting the DNA with SphI and the excised fragment was cloned in both orientations into the SphI site of M13mp19. These clones were digested at the KpnI and BamHI sites of the vector, treated with ExoIII and S1 nucleases and ligated, yielding a set of ordered deletions according to the method described in Henikoff, S., "Unidirectional digestion with exonuclease III creates targeted breakpoints for DNA sequencing", *Gene* 28:351–359 (1984), for DNA sequencing which was done using a Sequenase kit (US Biochemical Corporation).

To avoid band compressions due to high GC content, DITP was used in place of dGTP as suggested by the manufacturer. Samples were electrophoresed in 7M urea-6% acrylamide (acrylamide to bis acrylamide ration, 19:1) gels in 89 mM Tris-89 mM boric acid −2.5 mM EDTA, pH 8.3.

S1 Nuclease and Reverse Transcriptase Mapping

A clone containing bases 1–1354 of the strand encoding the bkd operon in M13mp19 was used to prepare radiolabelled, single-stranded DNA according to the method described in Aldea, M. et al. "Transcript mapping using [$^{35}$S]DNA probes, trichloroacetate solvent and dideoxy sequencing ladders: a rapid method for identification of transcriptional start points", *Gene* 65:101–110 (1988), to identify the start of transcription. A 17 mer universal primer was annealed to single-stranded DNA of the M13mp19 subclones and the complementary strand was synthesized using ($\alpha^{32}$P)dCTP, dNTPs and Klenow polymerase.

To minimize the amount of uncopied M13mp19 template, a 5 fold molar excess of primer and cold nucleotides were included in the synthesis reaction according to the method described in Calzone, F. J. et al., "Mapping of gene transcripts by nuclease protection assays and cDNA primer extension", *Methods Enzymol.* 152:611–632 (1987).

RNA (50 µg), extracted from *P. putida* grown in valine/isoleucine or glucose synthetic media and labelled DNA (10,000 cpm) were mixed in 30 µl of hybridization buffer (0.4M NaCl, 0.2M PIPES, pH 6.5, 5 mM EDTA, 80% formamide) according to Debarbouille, M., et al., "Expression of the *Escherichia coli* malPO operon remains unaffected after drastic alteration of its promoter", *J. Bacteriol.* 153:1221–1227 (1983). The solution was heated for 10 minutes at 75° C. and incubated at 40° C. overnight for hybridization of the DNA probe with branched chain keto acid dehydrogenase specific mRNA.

Unhybridized DNA was digested with 500 U of S1 nuclease in S1 buffer (0.25 N NaCl, 30 mM potassium acetate, pH 4.5, 1 mM ZnSO$_4$, 5% glycerol) at 40° C. for 1 hours. Nucleic acids were extracted with phenol, precipitated with ethanol and the pellet dissolved in deionized formamide and tracking dyes. The solution was heated to denature nucleic acids then loaded on a sequencing gel along with dideoxy sequencing ladders for precise sizing.

Reverse transcriptase mapping was carried out according to the method described in Shelness, G. S., et al., "Apolipoprotein II messenger RNA: Transcriptional and splicing heterogeneity yields six 5'- untranslated leader sequences", *J. Biol. Chem.*, 259:9929–9935 (1984). A synthetic oligonucleotide (Sequence ID No. 7) beginning 546 bp upstream of the branched chain keto acid dehydrogenase ATG initiation codon and complementary to the mRNA was used as primer. It was synthesized at the Molecular Biology Resource facility of the Saint Francis Hospital of Tulsa, Okla. The 5' end labelled primer (5,000–10,000 cpm) was combined with 50 µg of RNA from *P. putida* grown on valine/isoleucine in 50 µl of buffer (100 mM tris-HCl, pH 8.3, 10 mM MgCl$_2$, 120 mM KCl, 5 mM DTT, 1 mM deoxynucleotide triphosphates).

After the addition of 15 U of avian myelobastosis virus reverse transcriptase, samples were incubated for 1 hour at 42° C. and the reaction was stopped by bringing the temperature to 75° C. for 10 minutes. After cooling to 40° C., 5 µg of boiled RNAse A was added to this mixture and further incubated for 1 hour at 37° C. The nucleic acids were precipitated with ethanol and analyzed by electrophoresis as described above for S1 protection analysis.

Molecular Cloning

The insert containing the bkd promoter (Sequence ID No. 6) was excised from pJRS25 by digestion with SphI and inserted into pUC19. Two constructs were obtained, one with the insert in the same orientation as the lacZ, that is, the same as pJRS25, and a second, pJRS40, which had the insert in the opposite orientation to the lacZ.

In order to determine how much of the insert was required for promoter activity, a set of ordered deletions was prepared from these clones by digestion with ExoIII an S1 nucleases according to Henikoff, S., "Unidirectional digestion with exonuclease III creates targeted breakpoints for DNA sequencing", *Gene* 28:351–359 (1984). The inserts were excised from the multiple cloning sites of pUC19 by digestion with EcoRI and HindIII, isolated by agarose gel electrophoresis, and inserted into pKT240, also digested with EcoRI and HindIII.

*E. coli* DH5α was the host for transformation and transformants were selected using L-agar containing ampicillin. These constructs were transferred from *E. coli* DH5a to *P. putida* PpG2 by tri-parental mating according to the method described in Goldberg, J. B. et al., "Cloning and expression in *Pseudomonas aeruginosa* of a gene involved in the production of alginate", *J. Bacteriol.* 158: 1115–1121 (1984), and the exconjugants were plated on Pseudomonas isolation agar containing carbenicillin.

Clones with bkdA1 (Sequence ID No. 2) and bkdA2 (Sequence ID No. 3) as the reporter genes for the bkd promoter (Sequence ID No. 6) were constructed from pSO2, and 18 kb cosmid clone in pLAFR1 which contains the entire bkd operon (Sequence ID No. 1) plus 18 kb of flanking sequence according to the method described in S. K. Oh, M.S. thesis, University of Oklahoma Health Sciences Center, Oklahoma City, Okla., 1989. The cosmid, pSO2, was digested with SmaI releasing a 6.8 kb fragment containing the entire operon which was inserted into the SmaI site of pUC19, yielding pJRS51.

The insert was removed from pJRS51 by digestion with ClaI and BamHI. The ClaI site is at base 828 (FIG. 1) and the BamHI site is in the polylinker of pUC19. The ends of the insert were blunted with Klenow fragment and deoxynucleotide triphosphates and the fragment cloned into the SmaI site of pUC19. The resulting plasmid was digested with KpnI, which cuts into bkdB (Sequence ID No. 4), leaving bkdA1 (Sequence ID No. 2) and bkdA2 (Sequence ID No. 3) intact and into the polylinker upstream of the operon (FIG. 1).

Two constructs were obtained, pJRS43 with the promoter (Sequence ID No. 6), bkdA1 (Sequence ID No. 2) and bkdA2 (Sequence ID No. 3) in the opposite orientation as lacZ and pPJRS44, with the insert in the same orientation as lacZ. The inserts were then isolated from pUC19 by digestion with EcoRI and HindIII and inserted into pKT240 similarly digested. Again, two constructs were obtained, pJRS49, which has the insert in the opposite orientation to the aph gene and pJRS50 which has the insert in the same orientation as aph. The constructs were then transferred from E. coli DH5α to P. putida JS113 by tri-parental mating using pRK2013 according to the method described in Goldberg, J. B. et al., "Cloning and expression in Pseudomonas aeruginosa of a gene involved in the production of alginate", J. Bacteriol. 158:1115–1121 (1984).

Results

Isolation of bkd Promoter

A SphI genomic library of P. putida DNA in pUC19 was screened using a 1.45 kb nick-translated SstI-PstI fragment of P. putida DNA from pSS1-2 which contained all of bkdA1 (Sequence ID No. 2) and part of bkdA2 (Sequence ID No. 3)(FIG. 1) according to the method used in Burns, G. et al., "Similarity of the E1 subunits of branched chain-oxoacid dehydrogenase from Pseudomonas putida to the corresponding subunits of mammalian branched chain-oxoacid and pyruvate dehydrogenases", Eur. J. Biochem 176:311–317 (1988). Several positive colonies were identified during the initial screening which were further screened by restriction digestion of minipreparations, and Southern blotting usng the 1.45 kb probe. A clone containing 1.87 kb insert was obtained that contained 244 bp of bkdA1 (Sequence ID No. 2) gene and 1628 bp of upstream DNA. This clone was named pJRS25 and the restriction map of the insert is shown in FIG. 1.

Nucelotide Sequence of pJRS25 Insert

The nucleotide sequence of bases 721–1679 of pJRS25 is shown in Table 2. pJRS25 contains the bdk promoter (Sequence ID No. 6) at bases 728–1628, and the initial portion of bkdA1 (Sequence ID No. 2) from bases 1629–1674.

TABLE 2

```
 721 CACCCCACGGGCCATCTGCAGGCGGCGGCCTTCGAGAAAGCCTTCGGCGGTCATCACCTT
     GTGGGGTGCCCGGTAGACGTCCGCCGCCGGAAGCTCTTTCGGAAGCCGCCAGTA
        V  G  R  A  M  Q  L  R  R  G  E  L  F  G  E  A  T  M

781 GCCGCGTGGGACGCCGTTGAGGTCGGGGGTGACGCATTCGATTTCATCGATGCCCTGGAG

841 CTGAGCGATGCTCATGACGCTTGTCCTTGTTGTTGTAGGCTGACAACAACATAGGCTGGG
                          ─────>        <─────

901 GGTGTTTAAAATATCAAGCAGCCTCTCGAACGCCTGGGGCCTCTTCTATCGCGCAAGGTC

961 ATGCCATTGGCCGGCAACGGCAAGGCTGTCTTGTAGCGCACCTGTTTCAAGGCAAAACTC
                                *

1021 GAGCGGATATTCGCCACACCCGGCAACCGGGTCAGGTAATCGAGAAACCGCTCCAGCGCC

1081 TGGATACTCGGCAGCAGTACCCGCAACAGGTAGTCCGGGTCGCCCGTCATCAGGTAGCAC
                 ─────>                              ─────>

1141 TCCATCACCTCGGGCCGTTCGGCAATTTCTTCCTCGAAGCGGTGCAGCGACTGCTCTACC

1201 TGTTTTTCCAGGCTGACATGGATGAACACATTCACATCCAGCCCCAACGCCTCGGGCGAC

1261 AACAAGGTCACCTGCTGGCGGATCACCCCCAGTTCTTCCATGGCCCGCACCCGGTTGAAA
                                                    <─────

1321 CAGGGCGTGGGCGACAGGTTGACCGAGCGTGCCAGCTCGGCGTTGGTGATGCGGGCGTTT
     <─────

1381 TCCTGCAGGCTGTTGAGAATGCCGATATCGGTACGATCGAGTTTGCGCATGAGACAAAAT

1441 CACCGGTTTTTTGTGTTTATGCGGAATGTTTATCTGCCCCGCTCGGCAAAGGCAATCAAC
                  ─────>     ─────>

1501 TTGAGAGAAAAATTCTCCTGCCGGACCACTAAGATGTAGGGGACGCTGACTTACCAGTCA

1561 CAAGCCGGTACTCAGCGGCGGCCGCTTCAGAGCTCACAAAAACAAATACCCGAGCGAGCG
                                                              SD

1621 TAAAAAGCATGAACGAGTACGCCCCCCTGCGTTTGCATGTGCCCGAGCCCACCGGCCGG   1679
         M  N  E  Y  A  P  L  R  L  H  V  P  E  P  T  G  R
```

The codon for the initiating methionine of bkdA1 (Sequence ID No. 2) starts at position 1629 and the translated amino acid sequence matched exactly that of E1α (Sequence ID No. 2). The nucleotide sequence of the strand containing bkdA1 (Sequence ID No. 2) was translated in all three frames but no additional open reading frames were found on that strand which means that there is a large non-coding segment of DNA upstream of bkdA1 (Sequence ID No. 2)(Table 2).

There is a region of dyad symmetry from bases 868–876 and 883–891 with a modest, but probably significant free energy of formation of −14 kcal. Bases 280–286 of Sequence ID No. 1 repeat at bases 304–310 of Sequence ID No. 1, and there is another tandem repeat at bases 477–486 of Sequence ID No. 1 and bases 496–505 of Sequence ID No. 1.

There is a kind of symmetry beginning at bases 627–633 of Sequence ID No. 1 where the sequence is followed by its complement, bases 640–646 of Sequence ID No. 1. The GC content of the leader sequence (bases 775–1628, Table 2) is 56.7% which is distinctly lower than the 65.2% for the structural genes of the bkd operon (Sequence ID No. 1).

This agrees with the belief that RNA polymerase binds preferentially to AT rich regions of the promoter. A low GC content of the promoter region might also contribute to promoter strength by providing less resistance to DNA unwinding. Similar observations of low GC content for Pseudomonas promoter were made in the case of the algD and nah and sal promoters.

Figure 2:
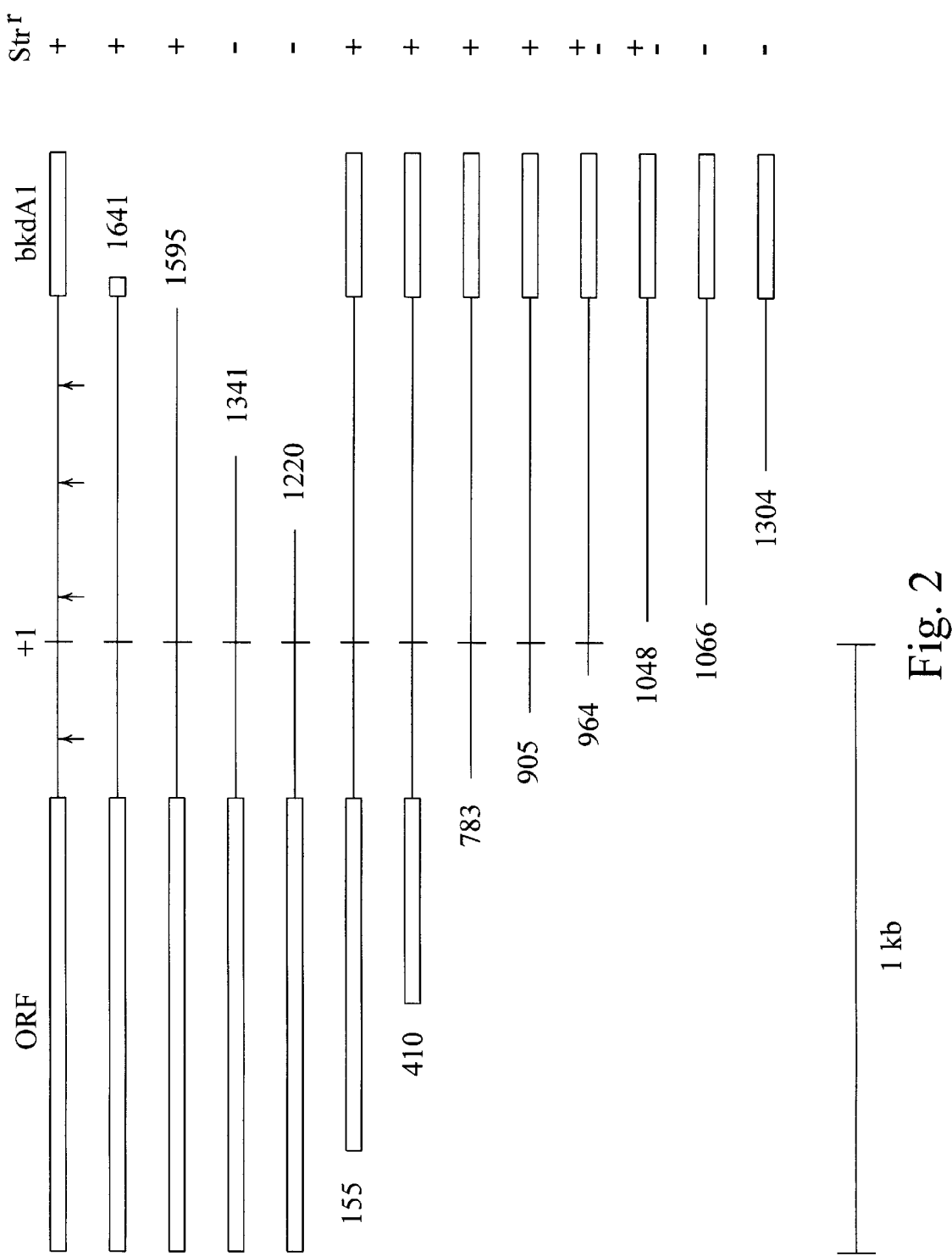
FIG. 2 shows the effect of deletions in the promoter region on bkd promoter (Sequence ID No. 6) activity. Streptomycin resistance was determined by growth on L-agar plus 8 mg streptomycin/ml. Numbers designated either the first (left) or last (right) base of the deletion clone as numbered in Table 2.

The strand opposite that encoding the branched chain keto acid dehydrogenase operon was translated into three reading frames and an open reading frame was found starting at 774 bp (FIG. 2). However, there does not seem to be a strong ribosome binding site preceding the start codon. This reading frame encoded 258 amino acids without a stop codon and the codon usage was consistent with that of other Pseudomonas genes.

The amino acid sequence was compared with the amino acid sequences of known regulatory proteins of bacteria in the Protein Information Resource data base, but no significant homology was found. However, a search by FASTP according to the method of Lipman, D. J. et al., "Rapid and sensitive protein similarity searches", *Science* 227:1435–1441 (1985), showed some homology with several glutamine synthetases ranging from 22–31% identity over a span of about 130 amino acids, and always to the same part of glutamine sythetase, residues 175–305.

Transcriptional Start of the bkd Operon (Sequence ID No. 1)

The approximate start of the bkd transcript was first determined by S1 nuclease protection experiments. A single-stranded DNA template in M13mp19 was constructed by ExoIII nuclease digestion according to the method described in Henikoff, S., "Unidirectional digestion with exonuclease III creates targeted breakpoints for DNA sequencing", *Gene* 28:351–359 (1984) which included bases 1–1354 of the pJRS25 insert. The M13 sequencing primer was annealed to the single-stranded DNA, and the complementary strand was synthesized using Klenow polymerase, dNTPs and $(\alpha^{32}P)dCTP$.

The radioactive DNA probe was hybridized to total cellular RNA extracted from *P. putida* grown in valine/isoleucine medium followed by treatment with a single-strand-specific S1 nuclease to destroy unprotected probe sequences according to the methods in Aldea, M., et al., "Transcript mapping using [$^{35}$S]DNA probes, trichloroacetate solvent and dideoxy sequencing ladders: a rapid method for identification of transcriptional start points", *Gene* 65:101–110 (1988) and Calzone, F. J., et al., "Mappng of gene transcripts by nuclease protection assays and cDNA primer extension", *Methods Enzymol.* 152:611–632 (1987).

These experiments show that the transcriptional start of the bkd operon (Sequence ID No. 1) was located about 600 bases upstream from the translational start. In order to locate the transcriptional start precisely, reverse transcriptase mapping was done by primer extension. A 15 mer oligonucleotide was constructed complementary to bases 1083–1097, i.e., 59 bp downstream from the start of transcription (Table 2). The end-labelled primer was hybridized to cellular RNA from *P. putida* PpG2 grown on valine/isoleucine medium and extended to the length of branched chain keto acid dehydrogenase mRNA with avian myeloblastosis virus reverse transcriptase.

The product was electrophoresed alongside dideoxy sequencing reaction mixtures using the same oligonucleotide primer (FIG. 2). A singles transcript was obtained, the mobility of which corresponded to base number 1037 of the pJRS25 insert. Therefore, the first base of the transcript is a cytidine nucleotide which means that the distance between the transcriptional and translational start is 592 bp.

In order to find the transcriptional initiation site of the message for the unknown open reading frame on the opposite strand, reverse transcriptase mapping was done using a 18 mer oligonucleotide that hybridized between 1097 and 1115 bp on the opposite strand (FIG. 2). The end-labelled oligonucleotide was annealed to RNA extracted from *P. putida* grown on L broth and minimal medium containing glucose or valine/isoleucine as the carbon sources.

No primer extension was evidenced after denaturing gel electrophoresis, indicating that there may not be a transcript or the transcript was not produced under the conditions which the cells were grown. Thus it is not clear if we are dealing with two promoters or if the bkd promoter is bidirectional.

Expression from the bkd Promoter (Sequence ID No. 6)

The promoter activity of the insert of *P. putida* DNA in pJRS25 was studied using pKT240 which has a promoter-less aminoglycoside phosphotransferase (aph) gene. When a DNA fragment containing a promoter is cloned in the correct orientation upstream of the aph gene, the host cell becomes streptomycin resistant.

The entire insert of pJRS25 was cloned into pKT240 in both orientations yielding pJRS47, with the insert opposed to aph, and pJRS48, with the insert in the same orientation as aph (Table 1). *E. coli* DH5α containing either pJRS47 or pJRS48 did not grow on L agar containing streptomycin at concentrations of 0.3 to 0.5 mg/ml indicating that *E. coli* does not read the bkd promoter (Sequence ID No. 6) well.

pJRS47 and pJRS48 were then mobilized from *E. coli* DH5α to *P. putida* PpG2 by tri-parental mating according to the method described in Goldberg, J. B. et al., "Cloning and expression in *Pseudomonas aeruginosa* of a gene involved in the production of alginate", *J. Bacteriol.* 158: 115–1121 (1984). The exconjugants were replica-plated on minimal medium containing valine/isoleucine or glucose as the carbon source plus various concentrations of streptomycin.

*P. putida* PpG2 containing either pJRS47 or pJRS48 was resistant to streptomycin at concentrations up to 10 mg/ml in both enriched and minimal media with either glucose or valine/isoleucine carbon sources. These results indicate the promoter was read in both directions and that streptomycin resistance was constitutive (FIG. 2). The finding that streptomycin resistance was not inducible strongly favors negative regulation of the bkd operon (Sequence ID No. 1).

*E. coli* DH5α and *P. putida* PpG2 (pKT240) did not grow at streptomycin concentrations beyond 0.25 and 2 mg/ml respectively. Expression of streptomycin resistance from pJRS47 was not expected, and this result suggests the presence of another promoter, possibly for the expression of the unidentified open reading frame on the strand opposite that of the bkd operon (Sequence ID No. 1) or that the bkd promoter (Sequence ID No. 6) is bidirectional.

A series of ordered deletions were created where the insert isolated from pJRS25 was shortened from both ends and then introduced into pKT240 to see what effect this had on promoter activity (FIG. 2). There is a span of about 550 bp which is essential from promoter activity in *P. putida* which begins 100 bp upstream of the start of transcription and ends 450 bp downstream from the start of transcription.

The two tandem repeats and the one dyad repeat downstream of the start are included in this essential region. However, the dyad repeat about 200 bp upstream of the start of transcription is not included. Perhaps this latter structure is involved in the expression of the unidentified open reading frame.

Expression of the bkd Operon (Sequence ID No. 1) Does Not Require the rpoN Gene Product Four deletion clones were mobilized into *P. putida* KT2440 and into the rpoN mutant. Two of the clones, those beginning at bases 783 and 905 (FIG. 2) conferred streptomycin resistance to both *P. putida* KT2440 and it rpoN mutant. The other two clones, those beginning at bases 1086 and 1304 (FIG. 2) failed to confer streptomycin resistance to either strain of *P. putida* KT2440.

In addition, the rpoN mutant of *P. putida* KT2440 is able to grow in synthetic medium with 2-ketoisovalerate as the sole carbon source, so it is clear that the rpoN sigma factor is not required for expression of branched chain keto acid dehydrogenase. As a control, it was confirmed that the rpoN mutant cannot grow in medium with valine/isoleucine as the carbon source, hence RpoN is required either for transport or transamination of branched chain amino acids.

Expression of bkdA1 (Sequence ID No. 2) and bkdA2 (Sequence ID No. 3) from the bkd Promoter (Sequence ID No. 6)

In order to study the expression of the bkd operon (Sequence ID No. 1), pJRS49 and pJRS50 were constructed (FIG. 1) which contain the bkd promoter (Sequence ID No. 6), bkdA1 (Sequence ID No. 2), and bkdA2 (Sequence ID No. 3) and part of bkdB (Sequence ID No. 4) in both orientations with respect to aph of pKT240. In these constructs, streptomycin resistance depends on the strength of the promoter upstream of aph and all are carbenicillin resistant due to the β-lactamase gene which is constitutively expressed.

pJRS43 and pJRS44 were transferred to *P. putida* JS113, a bkdA mutant, and plated on several media. *P. putida* JS113, a bkdA mutant, and plated on several media. *P. putida* JS113 containing either pJRS49 or pJRS50 grew on L-agar plus 8 mg/ml of streptomycin, however, *P. putida* JS113 (pJRS50), was more resistant to streptomycin than *P. putida* carrying pJRS49. These results show that read-through to aph occurred in both orientations.

*P. putida* JS113 (pJRS50) grew on valine/isoleucine agar plus streptomycin therefore the insert complemented the mutation in *P. putida* JS113. However, *P. putida* JS113 (pJRS49) did not grow on valine/isoleucine agar containing either carbenicillin or streptomycin for reasons which are not clear, but may be related to interference by these antibiotics with expression of the clone bkd genes.

In order to measure the level of expression of bkdA1 (Sequence ID No. 2) and bkdA2 (Sequence ID No. 3) from the bkd promoter (Sequence ID No. 6), E1 enzyme assays were performed on 90,000×g supernatant fractions prepared from cultures grown in the media shown in Table 3.

TABLE 3

Expression of structural genes for E1 subunits
(Sequence ID No. 2 and Sequence ID No. 3)
of *P. putida* branched chain keto acid dehydrogenase.

| Organism and | Plasmid | | |
|---|---|---|---|
| | | Specific activity[b] | |
| medium[a] | pKT240 | pJRS50 | pJRS49 |
| *E. coli* DH5α | | | |
| GASV | 0 | 0.014 | 0.018 |
| *P. putida* JS113 | | | |
| L broth | 0.009 | 2.37 | 2.59 |

TABLE 3-continued

Expression of structural genes for E1 subunits
(Sequence ID No. 2 and Sequence ID No. 3)
of *P. putida* branched chain keto acid dehydrogenase.

| Organism and | Plasmid | | |
|---|---|---|---|
| | | Specific activity[b] | |
| medium[a] | pKT240 | pJRS50 | pJRS49 |
| L broth + valine/ isoleucine | 0.0007 | 2.68 | 1.50 |
| Minimal medium + valine/ isoleucine | ND[c] | 5.23 | ND[c] |
| Minimal medium + glucose | 0.004 | 0.133 | 0.10 |

[a]Compositions of media are given in Materials and Methods.
[b]Specific activity is μmoles of NADH/min/mg protein. All assays of E1 (Sequence ID No. 2 and Sequence ID No. 3) were done by supplementing with excess E2 (Sequence ID No. 4) and LPD-val (Sequence ID No. 5).
[c]Does not grow in this medium.
[d]The specific activities of *P. putida* grown in L broth, L broth + valine/ isoleucine, minimal medium + glucose and minimal medium + valine/ isoleucine were 0.010, 0.010, 0.004 and 0.063 respectively. Extracts of *P. putida* PpG2 (pKT240) and *P. putida* PgG2 (pJRS48) in L broth gave specific activities of 0.032 and 0.033 respectively.

There was very little expression of bkdA1 (Sequence ID No. 2) and bkdA2 (Sequence ID No. 3) in *E. coli* DH5α containing either pJRS49 or pJRS50. However, there was high expression of bkdA1 (Sequence ID No. 2) and bkdA2 (Sequence ID No. 3) in *P. putida* JS113 containing either pJRS49 or pJRS50 grown in L-broth indicating that expression was constitutive as was streptomycin resistance in the case of *P. putida* PpG2 (pJRS48).

The level of E1 (Sequence ID No. 2 and Sequence ID No. 3) activity was surprisingly high compared to extracts of *P. putida* PpG2 grown in Valine/sioleucine medium (Table 3). Thus expression of bkdA1 (Sequence ID No. 2) and bkdA2 (Sequence ID No. 3) from *P. putida* JS113 (pJRS50) was nearly 40 times that obtained in *P. putida* PpG2 which seems to be much higher than could be accounted for by copy number alone.

When *P. putida* JS113 (pJRS50) was grown in valine/ isoleucine medium, the specific activity was about twice that obtained in L-broth. These results also suggest that the bkd operon (Sequence ID No. 1) is negatively regulated, probably by a small amount of endogeneous repressor which is titrated by the multiple copies of pJRS50 in the cell.

Again, *P. putida* JS113 (pJRS49), did not grow in this medium suggesting that bkdA1 (Sequence ID No. 2) and bkdA2 (Sequence ID No. 3) were not expressed. bkdA1 (Sequence ID No. 2) and bkdA2 (Sequence ID No. 3) expression was repressed by glucose (Table 3). It is pertinent to note that pseudomonads do not contain appreciable amounts of cAMP.

EXAMPLE 2

Materials and Methods

Bacterial strains and plasmids. The *P. putida* strains and plasmids used in this study are listed in Table 4.

TABLE 4

Strains of *P. putida*

| Strain and plasmid | Genotype[a] or description | Source |
|---|---|---|
| *P. putida* | | |
| PpG2 | Wild type | I. C. Gunsalus |
| JS112 | bkdAB lpdV (Sequence ID Nos. 2, 3, 4, and 5) | Sykes, P. J., et al., "Conjugative mapping of pyruvate, 2-ketoglutarate, and branched chain keto acid dehydrogenase genes in *Pseudomonasputida* mutants." J. Bacteriol. 162:203–208 (1985) |
| JS113 | bkdA (Sequence ID No. 1 and (Sequence ID No. 2) | Sykes, P. J., et al., "Conjugative mapping of pyruvate, 2-ketoglutarate, and branched chain keto acid dehydrogenase genes in *Pseudomonasputida* mutants." J. Bacteriol. 162:203–208 (1985) |
| JS287 | lpdV (Sequence ID No. 5) | Sokatch, J. R., et al., "Mutations affecting lipoamide dehydrogenases of *Pseudomonas putida*." J. Bacteriol. 153:969–975 (1983) |
| JS326 | bkdAB lpdV (Sequence ID Nos. 2, 3, 4, and 5) | Sykes, P. J., et al., "Conjugative mapping of pyruvate, 2-ketoglutarate, and branched chain keto acid dehydrogenase genes in *Pseudomonasputida* mutants." J. Bacteriol. 162:203–208 (1985) |
| PRS2003 | pKT230 catB Kan[r] Str[r] | M. Shanley |
| Plasmids | | |
| pKT230 | Derived from RSF1010 and pACYC1771 | Basdarian, M. et al. "Specific purpose plasmid cloning vectors II. Broad host range, copy number RSF 1010 - derived vectors, and a host-vector system fro gene cloning Pseudomonas", Gene 16:237–247 (1981). |
| pJRS1 | bkdAB lpdV (Sequence ID Nos. 2, 3, 4, and 5) in pUC18 | described herein |
| pJRS2 | bkdAB lpdV (Sequence ID Nos. 2, 3, 4, and 5) in pUC19 | described herein |
| pJRS3 | bkdB lpdV (Sequence ID Nos. 2, 3, 4, and 5) in pUC19 | described herein |
| pJRS4 | bkdAB lpdV (Sequence ID Nos. 2, 3, 4, and 5) in pUC18 | described herein |
| pJRS10 | bkdA (Sequence ID No. 1 and Sequence ID No. 2) in pUC18 | described herein |
| pJRS23 | lpdV (Sequence ID No. 5) in pUC18 | described herein |
| pJRS24 | bkdB (Sequence ID No. 4) in pUC19 | described herein |

[a]Gene designations for strains and plasmids in this table are bkdAB, E1 and E2 subunits of branched chain keto acid dehydrogenase; lpdV, LPD-Val (E3 subunit); catB, cis,cis-muconate lactonizing enzyme; Kan, kanamycin; Str, streptomycin.

Branched chain keto acid dehydrogenase mutants listed in Table 4 cannot grow on the valine-isoleucine agar described in the next paragraph. The strains of *E. coli* used were JM109 [Yanish-Perron, C., et al., "Improved M13 phage cloning vectors and host strains: nucleotide sequences of the M13mp18 and pUC19 vectors", *Gene.* 33:103–119 (1985)], HB101 [Boyer, H. W. et al., "A complementary analysis of the restriction and modifications of DNA in *Escherichia coli*", *J. Mol. Biol.* 141:459–427 (1969)], and TB1 which was obtained from Bethesda Research Laboratories, Inc. (Gaithersburg, Md.). TB1 is similar to JM83 except that TB1 is hsdr hsdM[+]. The plasmid vector pKT230 was described by Bagdasarian et al., "Specific purpose plasmid cloning vectors," *Gene* 16:237–247 (1981) and was provided by Mark Shanley, Department of Biology, Yale University.

Media. Valine-isoleucine agar contained 0.3% L-valine and 0.1% L-isoleucine in the basal medium as described in Marshall, V. P., et al., "Regulation of valine catabolism in *Pseudomonas putida*." *J. Bacteriol.* 110:1073–1081 (1972). Basal medium free of ammonium ion was obtained by omitting ammonium sulfate from the basal G solution. To test the inducibility of subunits of the complex in organisms unable to grow on valine-isoleucine agar, we used GASV medium. GASV medium contains 10 mM glucose, 2 mM acetate, 2 mM succinate, 0.3% valine, and 0.1% isoleucine. Valine is deaminated to 2-ketoisovalerate, the inducer of branched chain keto acid dehydrogenase, allowing expression of branched chain keto acid dehydrogenase. GAS medium lacks valine and isoleucine and was used to grow keto acid dehydrogenase mutants which might require acetate or succinate for growth as described in Guest, J. R., "Aspects of the molecular biology of lipoamide dehydrogenase", *Adv. Neurol.* 21:219–244 (1978). L broth was used as described in Lennox, E. S., "Transduction of linked genetic characters of the host of phage P1. "*Virology.* 1:190–206 (1955) and 2×YT medium as described in Miller, J. H., "Experiments in molecular genetics." Cold Spring Harbor Laboratory, Cold Spring Harbor, N.Y. (1976). When antibiotic supplements were used, the final concentrations were (micrograms per milliliter): streptomycin, 100; kanamycin, 90; ampicillin, 200.

DNA preparation. pKT230 was isolated from *P. putida* PRS2003 grown in 800 ml of L broth plus kanamycin by using two successive cesium chloride-ethidium bromide centrifugations of cleared lysates by the method of Clewell, D. B., et al., "Properties of a supercoiled deoxyribonucleic acid-protein relaxation complex and strand specificity of the relaxation event", *Biochemistry* 9:4428–4440 (1970). *P.*

*putida* chromosomal DNA was isolated from a single cesium chloride-ethidium bromide centrifugation by the same method as for plasmid preparation with omission of the sodium chloride precipitation step. DNA restriction fragments were separated by electrophoresis in 0.8% agarose gel.

Cloning procedures. A limited digest of *P. putida* chromosomal DNA by EcoRI and SstI produced a majority of fragments in the 5- to 15-kilobase (kb) size range. This was mixed with a complete EcoRI-SstI digest of pKT230 with chromosome-to-vector DNA ratios of 10:1 and ligated with T4 ligase. EcoRI-SstI digestion of pKT230 inactivates the streptomycin resistance gene, but leaves the β-lactamase promoter, which controls this gene, intact. Recombinant plasmids were $Km^r$ and $Sm^s$. The amount of DNA used in the ligations and transformations ranged from 0.06 to 0.2 µg. Ligation was done in a total volume of 50 µl containing 2 U of T4 ligase, and the mixture was left overnight at 14° C. The transformation procedure used for *P. putida* was that described by Bagdasarian, M. et al., "Host: vector systems for gene cloning in Pseudomonas." *Curr. Top. Microbiol. Immunol.* 96:47–67 (1982). Direct selection for recombinant molecules was achieved by complementation of *P. putida* branched chain keto acid dehydrogenase mutants listed in Table 4 for growth on valine-isoleucine medium and sensitivity to streptomycin. pSS1 and pSS1-1, which are recombinant derivatives of pKT230, were created in this fashion.

pJRS1 was created by digesting pSS1-1 with SstI and inserting the fragment into pUC18 also digested with SstI (FIG. 3). pJRS2 was created by digesting pJRS1 with EcoRI and HindIII which cut into the polylinker of pUC18, removing the insert of *P. putida* DNA which was ligated into pUC19 similarly digested. This procedure produced plasmids with inserts of *P. putida* DNA in opposite orientations.

pJRS3 was constructed from a PstI-SalI digest of pJRS2, and the resulting fragment was inserted into the polylinker of pUC19.

pJRS4 was constructed from pJRS1 by digestion with EcoRI and ClaI, which released a 6-kb fragment and left 1.8 kb of DNA still attached to pUC18. The 1.8-kb fragment was released by digestion with AccI which also created a sticky end in the polylinker compatible with ClaI. The 6-kb fragment was then ligated into pUC18 with EcoRI-ClaI sticky ends, yielding pJRS4.

pJRS10 was created by digestion of pJRS1 with KpnI which removed 4.5 kp of *P. putida* DNA. The remaining DNA (pUC18 plus insert of 3.3 kb) was then religated, yielding pJRS10.

pJRS23 was made by digesting the *P. putida* DNA insert of pJRS1 with Bal 31 so that deletions were created from the SstI restriction site at the E1 end of the coding region according to the method of Gilmore, M. S., et al., "A new strategy for ordered DNA sequencing based on a newer method for the rapid purification of near-milligram quantities of a cloned restriction fragment", *Gene Anal. Tech.* 2:108–114 (1985). The resulting DNA fragment contained a blunt end and a HindIII sticky end which was ligated into pUC18. This plasmid, pJRS21, was cut with SalI and EcoRI which released 2.3 kb of DNA. The remaining 2.9 kb of DNA was ligated into pUC18.

pJRS24 was obtained by digesting the polylinker of pJRS3 with BamHI and SstI and treating with ExoIII and S1 nucleases according to the method of Henikoff, S., "Unidirectional digestion with exonuclease III creates targeted breakpoints for DNA sequencing", *Gene* 28:351–359 (1984) and recircularizing the shortened plasmid with T4 ligase. The 3' overhang left by SstI protected the vector from digestion with ExoIII, while the 5' overhang left by BamHI allowed pJRS3 to be shortened from the E3 end, leaving only the E2 gene.

Genomic DNA-plasmid DNA hybridizations were done as described by Southern, E. M., "Detection of specific sequences among DNA fragments separated by gel electrophoresis." *J. Mol. Biol.* 98:503–517 (1975), using 0.33 µg of pSS1-1, pJRS1, or pJRS2 ($1.3 \times 10^7$ cpm/µg) and 5 to 6 µg of *E. coli*, *P. aeruginosa*, or *P. putida* DNA digested with EcoRI. To reduce hybridization with vector DNA, we included 0.6 µg of cold pKT230 or pUC18.

Minicells. The minicell strain used in these experiments was *E. coli* x925 which was obtained from Roy Curtiss. The experiment was performed essentially as described by Clarke-Curtiss, J. E., et al., "Analysis of recombinant DNA using *Escherichia coli* minicells." *Methods Enzymol.* 101:347–362 (1983), using 5 µCi of [$^{35}$S]methionine and with electrophoresis in 7.5% cross-linked polyacrylamide. Minicell cultures were grown in GASV medium since *E. coli* does not grow in valine-isoleucine medium.

In vitro transcription-translation. The procaryotic DNA-directed translation kit was purchased from Amersham and used as described in their instructions with 2.5 µg of DNA template for each reaction.

Enzyme assays. Preparation of extracts and the assays for branched chain keto acid dehydrogenase and lipoamide dehydrogenase have been described previously. The E1 (Sequence ID No. 2 and Sequence ID No. 3) and E2 (Sequence ID No. 4) assays were performed according to the method described in Sykes, P. J., et al., "Conjugative mapping of pyruvate, 2-ketoglutarate, and branched chain keto acid dehydrogenase genes in *Pseudomonas putida* mutants", *J. Bacteriol.* 162:203–208 (1985), and McCully, V. et al., "Resolution of branched chain oxo acid dehydrogenase complex of *Pseudomonas aeruginosa* PAO", *Biochem. J.* 233:737–742 (1986).

Stability of pSS1-1 in *P. putida*. Cultures of strain JS287 transformed with pKT230 and pSS1-1 were grown overnight in 4 ml of L broth plus kanamycin, and 0.1 ml of this culture was used to inoculate another 4 ml of L broth without kanamycin. Dilutions of overnight cultures were plated onto L agar, and resulting colonies were replica plated onto valine-isoleucine agar, valine-isoleucine agar plus kanamycin, and L agar plus kanamycin. Colonies growing on valine-isoleucine agar plus kanamycin were scored as carrying pSS1-1, colonies growing on valine-isoleucine agar without kanamycin were revertants, and those growing on L agar plus kanamycin but not valine-isoleucine agar plus kanamycin were carrying pKT230. These numbers were compared with the total number of colonies growing on L agar without kanamycin which included cells which had lost their plasmids.

Results

Figure 3:
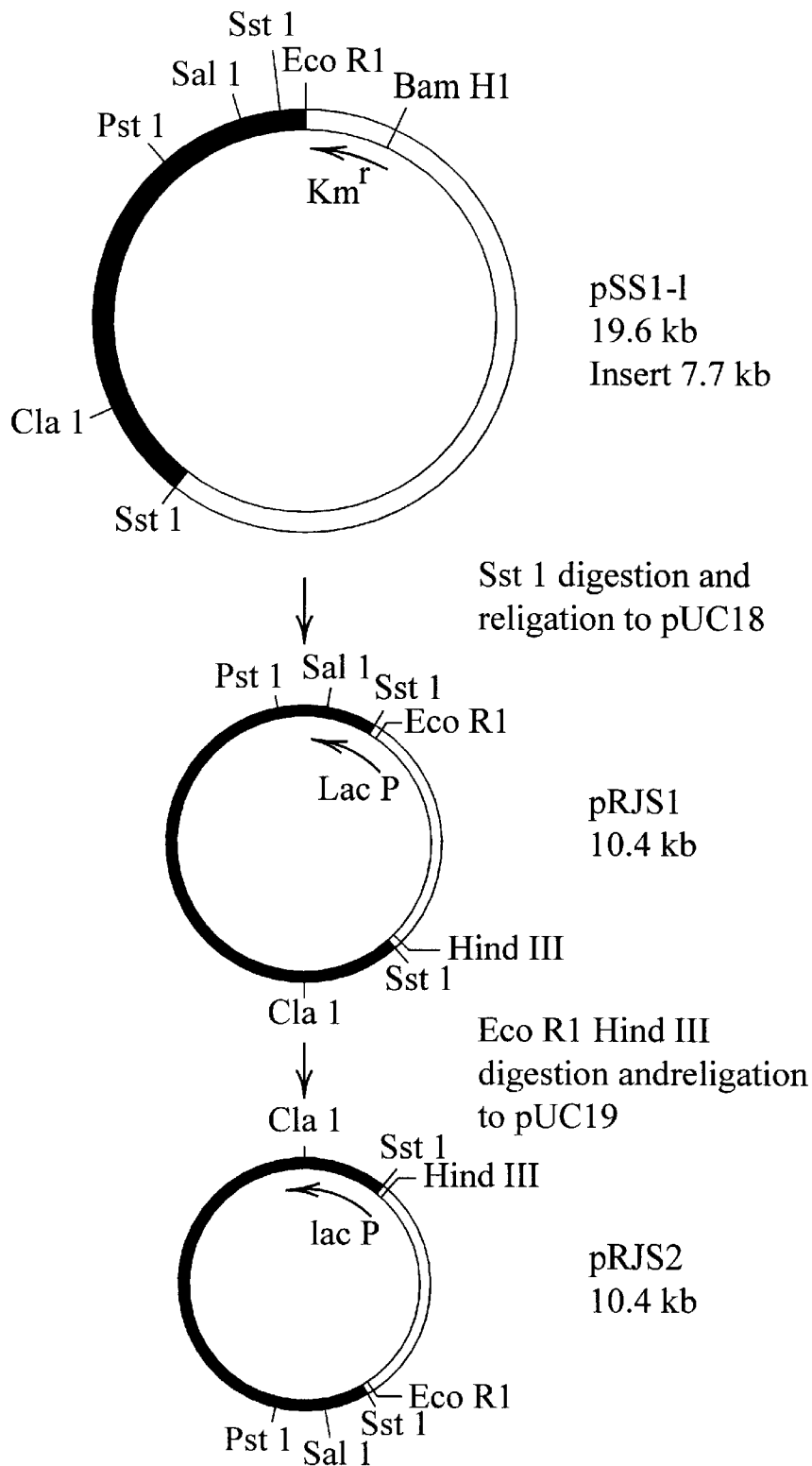
FIG. 3 shows the subcloning protocol used to isolate pJRS1 and pJRS2 with the insert of *P. putida* DNA in opposite orientations.

Cloning strategy. The vector used in these studies was pKT230, a broad-host-range plasmid of 11.9 kb able to replicate in *P. putida* and *E. coli*. Direct selection for recombinant molecules containing structural genes for subunits of branched chain keto acid dehydrogenase was achieved by complementation of *P. putida* branched chain keto acid dehydrogenase mutants. Complementation was detected by the ability of transformed mutants to grow on valine-isoleucine agar. Directed cloning with EcoRI-SstI digests yielded colonies on L agar plus kanamycin after transformation, 50 to 60% of which were $Str^s$ as a consequence of cloning into the streptomycin site. Direct plating of the transformation mixture onto valine-isoleucine agar yielded several colonies, one of which contained a plasmid with an insert of 11 kb and complemented strains JS112, JS113, JS326, and JS287. The results suggested that the plasmid, designated pSS1, contained all the structural genes for branched chain keto acid dehydrogenase.

pSS1 was subcloned by religation of a limited SalI digest which removed a 3.3-kb segment of DNA. The resulting plasmid, pSS1-1, also complemented all branched chain keto acid dehydrogenase mutants. pSS1-1 DNA hybridized with DNA from *P. putida* and *P. aeruginosa,* but not with DNA from *E. coli.* The insert was subcloned in pUC18 and pUC19 with the objective of determining the direction of transcription. The resulting plasmids were named pJRS1 and pJRS2, respectively (FIG. 3).

Stability of pDSS1-1 in *P. putida.* The stability of pSS1-1 in *P. putida* was determined by subculturing in L broth with or without kanamycin. All colonies of *P. putida* JS287 (pKT230) were Kan$^r$ after 11 serial transfers, showing that pKT230 was fully retained. However, strain JS287(pSS1-1) maintained the plasmid for three serial transfers after which kanamycin-sensitive, valine-isoleucine-negative colonies appeared, and by the eleventh transfer, only 3% of the colonies were kanamycin positive.

Expression of structural genes of pSS1-1 in *P. putida* mutants. Several pieces of data led to the conclusion that pSS1-1 contained structural genes for all subunits of branched chain keto acid dehydrogenase. The presence of pSS1-1 resulted in production of branched chain keto acid dehydrogenase activity in mutants lacking E1 (JS113); E1 (Sequence ID No. 2 and Sequence ID No. 3), E2, and LPD-Val (Sequence ID Nos. 2 and 3, Sequence ID No. 4, and Sequence ID No. 5, respectively) (JS326); and LPD-Val (Sequence ID No. 5) (JS287) (Table 5).

TABLE 5

Branched chain keto acid dehydrogenase activities of *P. putida* mutants transformed with pSS1-1

| Strain | Plasmid | Sp act of branched chain keto acid dehydrogenase[a] |
|---|---|---|
| JS113 | pKT230 | 0 |
| JS113 | pSS1-1 | 142 |
| JS326 | pKT230 | 1 |
| JS236 | pSS1-1 | 94 |
| JS287 | pKT230 | 4 |
| JS287 | pSS1-1 | 160 |

[a]The specific activity of branched chain keto acid dehydrogenase is nanomoles of NAD reduced per minute per milligram of protein. Cultures were grown in GASV medium.

For comparison, the specific activities of *P. putida* PpG2 (pKT230) and *P. putida* PpG2(pSS1-1) grown in valine-isoleucine medium were 54 and 314 nmol of NADH produced per min per mg of protein, respectively. *P. putida* mutants transformed with pKT230 did not regain branched chain keto acid dehydrogenase activity. The presence of all three subunits of branched chain keto acid dehydrogenase was demonstrated in mutants of *P. putida* (pSS1-1) by enzyme assays for E1 (Sequence ID No. 2 and Sequence ID No. 3) and E2 (Sequence ID No. 4) and by precipitation of LPD-Val (Sequence ID No. 5) with specific antisera. When the complex was purified from *P. putida* JS112(pSS1-1) it contained four polypeptides with the same molecular weights as complex purified from the wild type.

Regulation of branched chain keto acid dehydrogenase formation. Branched chain keto acid dehydrogenase activity was regulated by limitation of ammonium ion and by catabolite repression in *P. putida* PpG2 (Table 6).

TABLE 6

Nitrogen control of branched chain keto acid dehydrogenase synthesis

| Additions to valine-isoleucine medium | | | Sp act of branched chain keto acid dehydrogenase[a] |
|---|---|---|---|
| 40 mM NH$_4$ | 20 mM glucose | 30 mM succinate | |
| *P. putida* PpG2 | | | |
| + | − | − | 53 |
| − | − | − | 65 |
| + | + | − | 12 |
| − | + | − | 34 |
| + | − | + | 20 |
| − | − | + | 31 |
| *P. putida* JS112 (pSS1-1) | | | |
| + | − | − | 234 |
| − | − | − | 206 |
| + | + | − | 202 |
| − | + | − | 151 |
| + | − | + | 266 |
| − | − | + | 265 |

[a]The specific activity of branched chain keto acid dehydrogenase is nanomoles of NAD reduced per minute per milligram of protein. Cultures were grown in GASV medium.

Valine-isoleucine medium, which contained 40 mM ammonium ion, was used to obtain the data in Table 6. Where indicated, ammonium ion was deleted from the salt solution, leaving valine and isoleucine as the nitrogen sources. The presence of ammonium ion repressed complex formation, in particular, when supplemented with glucose. This is the typical situation for metabolism of N-containing compounds by gram-negative bacteria. Glucose and succinate also repressed branched chain keto acid dehydrogenase formation compared with that of control cells grown on valine-isoleucine medium. In contrast, neither the source of nitrogen nor the presence of glucose or succinate had any effect on complex formation by *P. putida* JS112(pSS1-1) which produced branched chain keto acid dehydrogenase constitutively. All other mutants of *P. putida* transformed with pSS1-1 also produced branched chain keto acid dehydrogenase constitutively.

Expression of branched chain keto acid dehydrogenase in *E. coli. E. coli* does not grow in media containing branched chain amino acids as the carbon sources. Therefore, production of branched chain keto acid dehydrogenase by *E. coli* carrying pSS1-1 would be evidence that structural genes had been cloned. *E. coli* HB101 was transformed with pKT230 and pSS1-1 and grown in GAS and GASV media, and cell extracts were examined for branched chain keto acid dehydrogenase. Surprisingly, the data in Table 7 show that *E. coli* HB101(pSS1-1) produced higher amounts of branched chain keto acid dehydrogenase in media containing valine.

TABLE 7

Expression of pSS1-1 structural genes in *E. coli* HB101

| | | Sp act | |
|---|---|---|---|
| Plasmid | Medium | E1[a] | Branched chain keto acid dehydrogense[b] |
| pKT230 | GAS | 0.0 | 0 |
| pKT230 | GASV | 0.4 | 0 |
| pSS1-1 | GAS | 7.7 | 7 |
| pSS1-1 | GASV | 20 | 48 |

[a]The specific activity is nanomoles of carbon dioxide released per 15 min per milligram of protein.
[b]The specific activity of branched chain keto acid dehydrogenase is nanomoles of NAD reduced per minute per milligram of protein. Cultures were grown in GASV medium.

This is also reflected in the specific activity of the E1 subunit (Sequence ID No. 2 and Sequence ID No. 3) which was nearly three times higher when HB101(pSS1-1) was grown in GASV medium compared with growth in GAS medium. It was not possible to measure E2 (Sequence ID No. 4) activity since *E. coli* contains a deacylase which gave a high endogenous rate with isobutyryl coenzyme A.

The data in Table 8 reinforce this result and show that relatively high amounts of L-valine are needed for induction of branched chain keto acid dehdrogenase in HB101(pSS1-1), while *P. putida* JS287(pSS1-1) produced branched chain keto acid dehydrogenase constitutively.

TABLE 8

Induction of branched chain keto acid dehydrogenase in *E. coli* HB101 (pSS1-1)

| | Sp act of branched chain keto acid dehydrogenase[a] in: | |
|---|---|---|
| Concn of L-valine in medium (mM) | *E. coli* HB101 (pSS1-1) | *P. putida* JS287 (pss1-1) |
| 0.0 | 12 | 300 |
| 0.1 | 14 | 296 |
| 0.5 | 11 | 325 |
| 2.0 | 7 | 264 |
| 10.0 | 38 | 231 |
| 25.0 | 112 | 234 |

[a]The specific activity of branched chain keto acid dehydrogenase is nanomoles of NAD reduced per minute per milligram of protein. Cultures were grown in GASV medium.

Extracts of *E. coli* HB101(pSS1-1) required coenzyme A for branched chain keto acid dehydrogenase activity and were slightly dependent on thiamine $PP_i$ and L-valine, although the latter dependence is difficult to demonstrate in cell extracts.

Expression in minicells. To demonstrate the production of branched chain keto acid dehydrogenase subunits, we transformed a minicell-producing strain, *E. coli* $_x$925, was transformed with pKT230 and pSS1-1. The minicells carrying pSS1-1 produced three radioactive peptides with molecular weights in sodium dodecyl sulfate-polyacrylamide gel electrophoresis of 39,000, 45,000, and 53,000 compared with molecular weights of 37,000, 39,000, 46,000, and 49,000 for the purified complex. Enzyme assays of cell extracts of *E. coli* $_x$925(pSS1-1) verified that branched chain keto acid dehydrogenase activity was present.

Expression of branched chain keto acid dehydrogenase from pJRS1 and pJRS2 templates. To resolve the problem of expression of branched chain keto acid dehydrogenase structural genes from pSS1-1 in minicells, *E. coli* JM109 was transformed with pJRS1 and pJRS2 which contained the insert of *P. putida* DNA in opposite orientations. *E. coli* JM109(pJRS1) produced large amounts of E1 (Sequence ID No. 2 and Sequence ID No. 3) and of branched chain keto acid dehydrogenase (Table 9).

TABLE 9

Expression of structural genes of pJRS1 and pJRS2 in *E. coli* JM109

| | Addition | Sp act | | |
|---|---|---|---|---|
| plasmid | to 2 x YT medium (mM) | E1[a] | Lipoamide dehydrogenase[b] | Branched chain keto acid dehydrogenase[c] |
| pUC18 | None | 1.5 | 190 | 0.0 |
| | Glucose (10) | ND[d] | 170 | 0.0 |
| | IPTG[e] (0.15) | 1.5 | 120 | 0.0 |
| pJRS1 | None | 141 | 1,700 | 130 |
| | Glucose (10) | 82 | 800 | 110 |
| | IPTG (0.15) | 191 | 1,800 | 150 |
| pJRS2 | None | 6.4 | 310 | 0.0 |
| | Glucose (10) | ND | 180 | 0.0 |
| | IPTG (0.15) | 4.0 | 400 | 0.6 |

[a]The specific activity of branched chain keto acid dehydrogenase is nanomoles of NAD reduced per minute per milligram of protein. Cultures were grown in GASV medium.
[b]The specific activity is nanomoles of NADH oxidized per minute per milligram of protein.
[c]The specific activity of branched chain keto acid dehydrogenase is nanomoles of NAD reduced per minute per milligram of protein. Cultures were grown in GASV medium.
[d]ND, Not determined.
[e]IPTG, Isopropyl-β-D-thiogalactopyranoside.

The formation of LPD-Val (Sequence ID No. 5) was demonstrated directly by the use of specific antiserum and indirectly by the greatly increased activity of lipoamide dehydrogenase in extracts of *E. coli* JM109(pJRS1). In contrast, *E. coli* JM109(pJRS2) produced negligible amounts of branched chain keto acid dehydrogenase (Table 9). The expression of branched chain keto acid dehydrogenase is clearly constitutive in *E. coli* JM109(pJRS1), although glucose had a slight repressive effect and isopropyl-β-D-thiogalactopyranoside appeared to have a slight inductive effect. However, failure of *E. coli* JM109 (pJRS2) to produce significant amounts of branched chain keto acid dehydrogenase indicated that it was the pUC promoter which was read by *E. coli* RNA polymerase.

pUC18, pJRS1, and pJRS2 were used as DNA templates in the in vitro procaryotic translation system to determine the size and number of transcripts on the *P. putida* DNA. With pJRS1 as the template, four polypeptides were produced with molecular weights of 37,000, 39,000, 47,000, and 49,000 which were superimposable on those from a purified preparation of branched chain keto acid dehydrogenase included as a control. When pJRS2 was the template, trace amounts of these same four polypeptides were produced, suggesting that Pseudomonas promoters were being read by *E. coli* RNA polymerase, although rather inefficiently. In this same experiment, pKT230, pSS1, and pSS1-1 were also used as DNA templates, but no radioactive proteins were formed other than those associated with pKT230.

Figure 4:
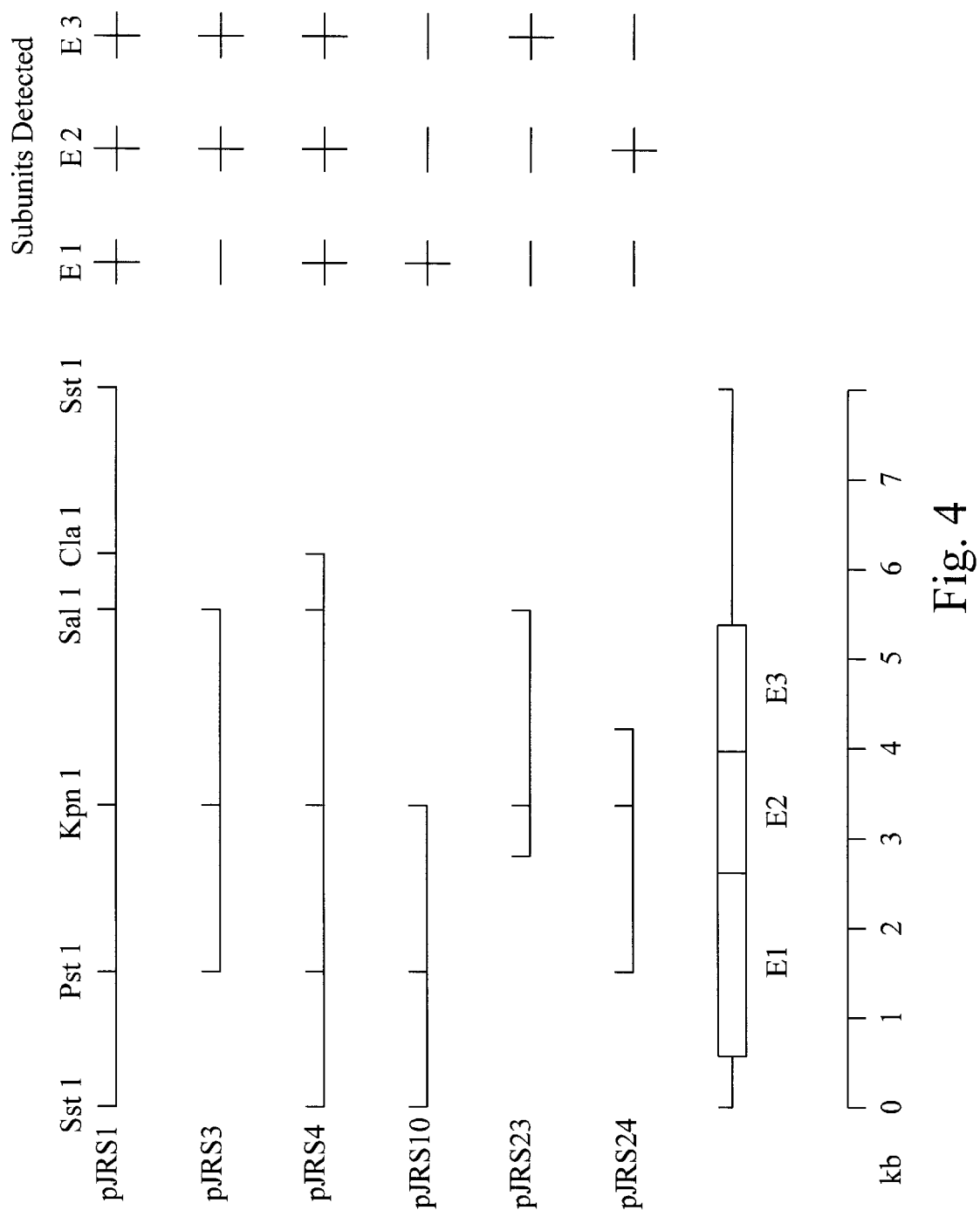
FIG. 4 shows the restriction maps of plasmids which contain structural genes for branched chain keto acid dehydrogenase THe N-terminal coding region is at the left, and the transcription is from left to right for all structural genes.

Location of structural genes. The location and order of structural genes for branched chain keto acid dehydrogenase were established by subcloning into pUC18 or pUC19 and identifying the gene products by the methods described below (FIG. 4). The N-terminal coding region of each gene is shown at the left of FIG. 4. The smallest fragment which contained all the structural genes was pJRS4, which is 6 kp in length. Extracts of *E. coli* TB1(pJRS4) contained branched chain keto acid dehydrogenase, and when pJRS4 was used as the DNA template in the transcription-translation system, four protein bands with the correct molecular weights were produced. pJRS10 contains the structural genes for the E1 subunit(s) (Sequence ID No. 2 and Sequence ID No. 3). Proteins with molecular weights of 37,000 and 39,000 were produced when pJRS10 was the template in the transcription-translation system. Also, extracts of *E. coli* TB1(pJRS10) supplemented the heat-treated Sepharose CL4B fraction which contains active E2 and E3 (Sequence ID No. 4 and Sequence ID No. 5, respectively) subunits, producing active branched chain keto acid dehydrogenase. pJRS23 contains the complete structural gene for LPD-Val (Sequence ID No. 5) which was established by showing that extracts of *E. coli* TB1(pJRS23) reacted with specific anti-LPD-Val serum and complemented extracts of *P. putida* JS287. pJRS24 contained only the structural genes for the E2 subunit since extracts of *E. coli* TB1(pJRS10) and purified LPD-Val yielded active branched chain keto acid dehydrogenase. No activity was obtained when extracts of *E. coli* TB1(pJRS10) and *E. coli* TB1(pJRS24) were mixed unless purified LPD-Val was added, showing that pJRS24 did not contain the structural gene for LPD-Val (Sequence ID No. 5).

EXAMPLE 3

An example of how to express foreign genes in *Pseudomonas putida* using the bkad promoter (Sequence ID No. 6) is to start with plasmid pJRS55 (ATCC #68403). In order to insert a gene, pJRS55 could be digested with SacI and the 11 kb fragment containing the promoter (Sequence ID No. 6) and leader isolated. The sticky ends could be blunted with Klenow Regent and deoxynucleoside triphosphates. This provides a restriction site behind the promoter (Sequence ID No. 6) and leader which can be used with any blunt-ended DNA fragment.

As an example of a gene that could be inserted, lpdV of *P. putida* could be removed from plasmid pJRS54 (#68405) by digestion with ScaI. This digest would release the entire lpdV gene (Sequence ID No. 5) in a blunt-ended fragment which can be ligated to the 11 kb promoter-leader fragment. This would provide a mixture of the desired plasmid plus a construct with the lpdV gene (Sequence ID No. 5) in the opposite orientation to the bkad promoter (Sequence ID No. 6). The ligation mixture could be used to transform *P. putida* which is placated on L-agar plus ampicillin. The correct construct could be identified by picking several colonies, isolating the plasmid and digesting it with several restriction enzymes in order to determine the orientation of the insert.

All patent applications and publications cited herein are hereby incorporated by reference into the present application.

Changes may be made in the embodiments of the invention described herein or in parts or elements of the embodiments described herein or in the steps or in the sequence of steps of the methods described herein without departing from the spirit and scope of the invention as defined in the following claims.

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
      (A) LENGTH: 6122 base pairs
      (B) TYPE: Nucleic acid
      (C) STRANDEDNESS: Double stranded
      (D) TOPOLOGY: Circular (ii) MOLECULE TYPE: Genomic DNA
      (A) DESCRIPTION: Seq ID No 1 is genomic DNA from P. putida
         strain PpG2 which contains the control region regulating
         expression of the bkd operon and the four structural
         genes of the bkd operon, bkdA1, bkdA2, bkdB and lpdV.

(iii) HYPOTHETICAL: No (iv) ANTI-SENSE: No (v) FRAGMENT TYPE: Not applicable (vi) ORIGINAL SOURCE:
      (A) ORGANISM: Pseudomonas putida
      (B) STRAIN: PpG2
      (C) INDIVIDUAL ISOLATE: Not applicable
      (D) DEVELOPMENTAL STAGE: Not applicable
      (E) HAPLOTYPE: Not applicable
      (F) TISSUE TYPE: Not applicable
      (G) CELL TYPE: Gram negative, aerobic bacilli
      (H) CELL LINE: Not applicable
      (I) ORGANELLE: Not applicable (vii) IMMEDIATE SOURCE:

```
        (A) LIBRARY: Genomic DNA from Pseudomonas putida
        (B) CLONE: pJRS54

(viii) POSITION IN GENOME:
        (A) CHROMOSOME/SEGMENT:
        (B) MAP POSITION: 35 Minutes
        (C) UNITS:

(ix) FEATURE:
        (A) NAME/KEY: Promoter plus leader
        (B) LOCATION: 1-792
        (C) IDENTIFICATION METHOD: By experiment
        (D) OTHER INFORMATION: The promoter plus leader are
            responsible for expression of the bkd operon in
            Pseudomonas putida (ix) FEATURE:
        (A) NAME/KEY: bkdA1, Gene encoding branched-chain keto acid
            dehydrogenase-decarboxylase E1 alpha subunit.
        (B) LOCATION: 805-2031. Initiating methionine codon is at
            position 802, however mature peptide does not contain N-
            terminal methionine.
        (C) IDENTIFICATION METHOD: By experiment
        (D) OTHER INFORMATION: The E1 component of branched chain keto
            acid dehydrogenase catalyzes the oxidative
            decarboxylation of the keto acid substrate. E1 is
            composed of two subunits, E1 alpha and E1 beta.

(ix) FEATURE:
        (A) NAME/KEY: bkdA2, Gene encoding branched-chain keto acid
            dehydrogenase-decarboxylase E1 beta subunit.
        (B) LOCATION: 2078-3091. Initiating methionine codon is
            position 2075, however mature peptide does not contain
            N-terminal methionine.
        (C) IDENTIFICATION METHOD: By experiment
        (D) OTHER INFORMATION: See description for Feature 2 above.

(ix) FEATURE:
        (A) NAME/KEY: bkdB Gene encoding the E2 component of branched
            chain keto acid dehydrogenase
        (B) LOCATION: 3098-4363 Initiating methionine codon is
            position 3095, however mature peptide does not contain
            N-terminal methionine.
        (C) IDENTIFICATION METHOD: By experiment
        (D) OTHER INFORMATION: E2 catalyzes the transacylation of the
            fatty acyl group from the lipoyl residue of E2 to
            coenzyme A. E2 is the core of the complex and binds E1
            and E3 components.

(ix) FEATURE:
        (A) NAME/KEY: lpdV, Gene encoding the E3 component of branched
            chain keto acid dehydrogenase.
        (B) LOCATION: 4369-5745. N-terminal methionine is present on
            mature peptide.
        (C) IDENTIFICATION METHOD: By experiment
        (D) OTHER INFORMATION: E3 is LPD-val, the specific lipoamide
            dehydrogenase which catalyzes oxidation of the
            dihydrolipoyl residue of the E2 component of branched
            chain keto acid dehydrogenase and the reduction of NAD+.

(x) PUBLICATION INFORMATION:
        (A) AUTHORS: Sokatch, John R.
            McCully, Vicki
            Gebrosky, Janet
            Sokatch, David,J.
        (B) TITLE: Isolation of a specific lipoamide dehydrogenase
            for a branched-chain keto acid dehydrogenase
            from Pseudomonas putida
        (C) JOURNAL: Journal of Bacteriology
        (D) VOLUME: 148
        (E) ISSUE:
        (F) PAGES: 639-646
        (G) DATE: 1981
        (A) AUTHORS: Sokatch,John R.
            McCully, Vicki
            Roberts, C.M.
        (B) TITLE: Purification of a branched-chain keto acid
            dehydrogenase from Pseudomonas putida
        (C) JOURNAL: Journal of Bacteriology
```

(D) VOLUME: 148
(E) ISSUE:
(F) PAGES: 647-652
(G) DATE: 1981
(A) AUTHORS: Sykes, Pamela
    Burns, Gayle
    Menard, Joan
    Hatter, Kenneth
    Sokatch, John R.
(B) TITLE: Molecular cloning of genes encoding branched-chain
    keto acid dehydrogenase of Pseudomonas putida
(C) JOURNAL: Journal of Bacteriology
(D) VOLUME: 169
(E) ISSUE:
(F) PAGES: 1619-1625
(G) DATE: 1987
(A) AUTHORS: Burns, Gayle
    Brown, Tracy
    Hatter, Kenneth
    Sokatch, John R.
(B) TITLE: Comparison of the amino acid sequences of the
    transacylase components of branched-chain oxoacid
    dehydrogenase of Pseudomonas putida, and the pyruvate
    and 2-oxoglutarate dehydrogenases of Escherichia coli
(C) JOURNAL: European Journal of Biochemistry
(D) VOLUME: 176
(E) ISSUE:
(F) PAGES: 165-169
(G) DATE: 1988
(A) AUTHORS: Burns,Gayle
    Brown, Tracy
    Hatter, Kenneth
    Idriss, John M.
    Sokatch, John R.
(B) TITLE: Similarity of the E1 subunits of branched-chain-
    oxoacid dehydrogenase from Pseudomonas putida to the
    corresponding subunits of mammalian branched-chain-
    oxoacid and pyruvate dehydrogenases
(C) JOURNAL: European Journal of Biochemistry
(D) VOLUME: 176
(E) ISSUE:
(F) PAGES: 311-317
(G) DATE: 1988
(A) AUTHORS: Burns, Gayle
    Brown, Tracy
    Hatter, Kenneth
    Sokatch, John R.
(B) TITLE: Sequence analysis of the lpdV gene for lipoamide
    dehydrogenase of Pseudomonas putida
(C) JOURNAL: European Journal of Biochemistry
(D) VOLUME: 179
(E) ISSUE:
(F) PAGES: 61-69
(G) DATE: 1989
(A) AUTHORS: Madhusudhan, K.T.
    Huang, G.
    Burns, Gayle
    Sokatch, J.R.
(B) TITLE: Transcriptional analysis of the promoter region of
    the branched chain keto acid dehydrogenase operon of
    Pseudomonas putida
(C) JOURNAL: Journal of Bacteriology
(D) VOLUME: 172
(E) ISSUE: October, 1990
(F) PAGES: 5655-5663
(G) DATE: 1990
(K) RELEVANT RESIDUES IN SEQ ID NO:1: FROM 1 TO 6122

(xi) SEQUENCE DESCRIPTION: SEQ ID NO:1:

```
CGATGCCCTG GAGCTGAGCG ATGCTCATGA CGCTTGTCCT TGTTGTTGTA GGCTGACAAC      60

AACATAGGCT GGGGGTGTTT AAAATATCAA GCAGCCTCTC GAACGCCTGG GGCCTCTTCT     120

ATCGCGCAAG GTCATGCCAT TGGCCGGCAA CGGCAAGGCT GTCTTGTAGC GCACCTGTTT     180

CAAGGCAAAA CTCGAGCGGA TATTCGCCAC ACCCGGCAAC CGGGTCAGGT AATCGAGAAA     240

CCGCTCCAGC GCCTGGATAC TCGGCAGCAG TACCCGCAAC AGGTAGTCCG GGTCGCCCGT     300
```

-continued

```
CATCAGGTAG CACTCCATCA CCTCGGGCCG TTCGGCAATT TCTTCCTCGA AGCGGTGCAG    360

CGACTGCTCT ACCTGTTTTT CCAGGCTGAC ATGGATGAAC ACATTCACAT CCAGCCCCAA    420

CGCCTCGGGC GACAACAAGG TCACCTGCTG GCGGATCACC CCCAGTTCTT CCATGGCCCG    480

CACCCGGTTG AAACAGGGCG TGGGCGACAG GTTGACCGAG CGTGCCAGCT CGGCGTTGGT    540

GATGCGGGCG TTTTCCTGCA GGCTGTTGAG AATGCCGATA TCGGTACGAT CGAGTTTGCG    600

CATGAGACAA ATCACCGGT TTTTTGTGTT TATGCGGAAT GTTTATCTGC CCCGCTCGGC    660

AAAGGCAATC AACTTGAGAG AAAAATTCTC CTGCCGGACC ACTAAGATGT AGGGGACGCT    720

GACTTACCAG TCACAAGCCG GTACTCAGCG GCGGCCGCTT CAGAGCTCAC AAAAACAAAT    780

ACCCGAGCGA GCGTAAAAAG CATG AAC GAG TAC GCC CCC CTG CGT TTG          828
                            Asn Glu Tyr Ala Pro Leu Arg Leu
                                            5

CAT GTG CCC GAG CCC ACC GGC CGG CCA GGC TGC CAG ACC GAT TTT TCC    876
His Val Pro Glu Pro Thr Gly Arg Pro Gly Cys Gln Thr Asp Phe Ser
 10              15                  20

TAC CTG CGC CTG AAC GAT GCA GGT CAA GCC CGT AAA CCC CCT GTC GAT    924
Tyr Leu Arg Leu Asn Asp Ala Gly Gln Ala Arg Lys Pro Pro Val Asp
 25              30                  35                      40

GTC GAC GCT GCC GAC ACC GCC GAC CTG TCC TAC AGC CTG GTC CGC GTG    972
Val Asp Ala Ala Asp Thr Ala Asp Leu Ser Tyr Ser Leu Val Arg Val
                 45                  50                  55

CTC GAC GAG CAA GGC GAC GCC CAA GGC CCG TGG GCT GAA GAC ATC GAC   1020
Leu Asp Glu Gln Gly Asp Ala Gln Gly Pro Trp Ala Glu Asp Ile Asp
             60                  65                  70

CCG CAG ATC CTG CGC CAA GGC ATG CGC GCC ATG CTC AAG ACG CGG ATC   1068
Pro Gln Ile Leu Arg Gln Gly Met Arg Ala Met Leu Lys Thr Arg Ile
         75                  80                  85

TTC GAC AGC CGC ATG GTG GTT GCC CAG CGC CAG AAG AAG ATG TCC TTC   1116
Phe Asp Ser Arg Met Val Val Ala Gln Arg Gln Lys Lys Met Ser Phe
     90                  95                 100

TAC ATG CAG AGC CTG GGC GAA GAA GCC ATC GGC AGC GGC CAG GCG CTG   1164
Tyr Met Gln Ser Leu Gly Glu Glu Ala Ile Gly Ser Gly Gln Ala Leu
105             110                 115                     120

GCG CTT AAC CGC ACC GAC ATG TGC TTC CCC ACC TAC CGT CAG CAA AGC   1212
Ala Leu Asn Arg Thr Asp Met Cys Phe Pro Thr Tyr Arg Gln Gln Ser
                125                 130                 135

ATC CTG ATG GCC CGC GAC GTG TCG CTG GTG GAG ATG ATC TGC CAG TTG   1260
Ile Leu Met Ala Arg Asp Val Ser Leu Val Glu Met Ile Cys Gln Leu
            140                 145                 150

CTG TCC AAC GAA CGC GAC CCC CTC AAG GGC CGC CAG CTG CCG ATC ATG   1308
Leu Ser Asn Glu Arg Asp Pro Leu Lys Gly Arg Gln Leu Pro Ile Met
        155                 160                 165

TAC TCG GTA CGC GAG GCC GGC TTC TTC ACC ATC AGC GGC AAC CTG GCG   1356
Tyr Ser Val Arg Glu Ala Gly Phe Phe Thr Ile Ser Gly Asn Leu Ala
    170                 175                 180

ACC CAG TTC GTG CAG GCG GTC GGC TGG GCC ATG GCC TCG GCG ATC AAG   1404
Thr Gln Phe Val Gln Ala Val Gly Trp Ala Met Ala Ser Ala Ile Lys
185                 190                 195                 200

GGC GAT ACC AAG ATT GCC TCG GCC TGG ATC GGC GAC GGC GCC ACT GCC   1452
Gly Asp Thr Lys Ile Ala Ser Ala Trp Ile Gly Asp Gly Ala Thr Ala
                205                 210                 215

GAA TCG GAC TTC CAC ACC GCC CTC ACC TTT GCC CAC GTT TAC CGC GCC   1500
Glu Ser Asp Phe His Thr Ala Leu Thr Phe Ala His Val Tyr Arg Ala
            220                 225                 230

CCG GTG ATC CTC AAC GTG GTC AAC AAC CAG TGG GCC ATC TCA ACC TTC   1548
Pro Val Ile Leu Asn Val Val Asn Asn Gln Trp Ala Ile Ser Thr Phe
```

-continued

```
              235                 240                 245
CAG GCC ATC GCC GGT GGC GAG TCG ACC ACC TTC GCC GGC CGT GGC GTG      1596
Gln Ala Ile Ala Gly Gly Glu Ser Thr Thr Phe Ala Gly Arg Gly Val
    250                 255                 260

GGC TGC GGC ATC GCT TCG CTG CGG GTG GAC GGC AAC GAC TTC GTC GCC      1644
Gly Cys Gly Ile Ala Ser Leu Arg Val Asp Gly Asn Asp Phe Val Ala
265                 270                 275                 280

GTT TAC GCC GCT TCG CGC TGG GCT GCC GAA CGT GCC CGC CGT GGT TTG      1692
Val Tyr Ala Ala Ser Arg Trp Ala Ala Glu Arg Ala Arg Arg Gly Leu
                285                 290                 295

GGC CCG AGC CTG ATC GAG TGG GTC ACC TAC CGT GCC GGC CCG CAC TCG      1740
Gly Pro Ser Leu Ile Glu Trp Val Thr Tyr Arg Ala Gly Pro His Ser
            300                 305                 310

ACC TCG GAC GAC CCG TCC AAG TAC CGC CCT GCC GAT GAC TGG AGC CAC      1788
Thr Ser Asp Asp Pro Ser Lys Tyr Arg Pro Ala Asp Asp Trp Ser His
        315                 320                 325

TTC CCG CTG GGT GAC CCG ATC GCC CGC CTG AAG CAG CAC CTG ATC AAG      1836
Phe Pro Leu Gly Asp Pro Ile Ala Arg Leu Lys Gln His Leu Ile Lys
    330                 335                 340

ATC GGC CAC TGG TGC GAA GAA GAA CAC CAG GCC ACC ACG GCC GAG TTC      1884
Ile Gly His Trp Cys Glu Glu Glu His Gln Ala Thr Thr Ala Glu Phe
345                 350                 355                 360

GAA GCG GCC GTG ATT GCT GCG CAA AAA GAA GCC GAG CAG TAC GGC ACC      1932
Glu Ala Ala Val Ile Ala Ala Gln Lys Glu Ala Glu Gln Tyr Gly Thr
                365                 370                 375

CTG GCC AAC GGT CAC ATC CCG AGC GCC GCC TCG ATG TTC GAG GAC GTG      1980
Leu Ala Asn Gly His Ile Pro Ser Ala Ala Ser Met Phe Glu Asp Val
            380                 385                 390

TAC AAG GAG ATG CCC GAC CAC CTG CGC CGC CAA CGC CAG GAA CTG GGG      2028
Tyr Lys Glu Met Pro Asp His Leu Arg Arg Gln Arg Gln Glu Leu Gly
        395                 400                 405

GTT TGAGATGAAC GACCACAACA ACAGCATCAA CCCGGAAACC GCCATG GCC ACC       2083
Val                                                   Ala Thr

ACT ACC ATG ACC ATG ATC CAG GCC CTG CGC TCG GCC ATG GAT GTC ATG      2131
Thr Thr Met Thr Met Ile Gln Ala Leu Arg Ser Ala Met Asp Val Met
        5                   10                  15

CTT GAG CGC GAC GAC AAT GTG GTG GTG TAC GGC CAG GAC GTC GGC TAC      2179
Leu Glu Arg Asp Asp Asn Val Val Val Tyr Gly Gln Asp Val Gly Tyr
    20                  25                  30

TTC GGC GGC GTG TTC CGC TGC ACC GAA GGC CTG CAG ACC AAG TAC GGC      2227
Phe Gly Gly Val Phe Arg Cys Thr Glu Gly Leu Gln Thr Lys Tyr Gly
35                  40                  45                  50

AAG TCC CGC GTG TTC GAC GCG CCC ATC TCT GAA AGC GGC ATC GTC GGC      2275
Lys Ser Arg Val Phe Asp Ala Pro Ile Ser Glu Ser Gly Ile Val Gly
                55                  60                  65

ACC GCC GTG GGC ATG GGT GCC TAC GGC CTG CGC CCG GTG GTG GAA ATC      2323
Thr Ala Val Gly Met Gly Ala Tyr Gly Leu Arg Pro Val Val Glu Ile
            70                  75                  80

CAG TTC GCT GAC TAC TTC TAC CCG GCC TCC GAC CAG ATC GTT TCT GAA      2371
Gln Phe Ala Asp Tyr Phe Tyr Pro Ala Ser Asp Gln Ile Val Ser Glu
        85                  90                  95

ATG GCC CGC CTG CGC TAC CGT TCG GCC GGC GAG TTC ATC GCC CCG CTG      2419
Met Ala Arg Leu Arg Tyr Arg Ser Ala Gly Glu Phe Ile Ala Pro Leu
    100                 105                 110

ACC CTG CGT ATG CCC TGC GGT GGC GGT ATC TAT GGC GGC CAG ACA CAC      2467
Thr Leu Arg Met Pro Cys Gly Gly Gly Ile Tyr Gly Gly Gln Thr His
115                 120                 125                 130

AGC CAG AGC CCG GAA GCG ATG TTC ACT CAG GTG TGC GGC CTG CGC ACC      2515
Ser Gln Ser Pro Glu Ala Met Phe Thr Gln Val Cys Gly Leu Arg Thr
```

-continued

```
              135                 140                 145
GTA ATG CCA TCC AAC CCG TAC GAC GCC AAA GGC CTG CTG ATT GCC TCG        2563
Val Met Pro Ser Asn Pro Tyr Asp Ala Lys Gly Leu Leu Ile Ala Ser
            150                 155                 160

ATC GAA TGC GAC GAC CCG GTG ATC TTC CTG GAG CCC AAG CGC CTG TAC        2611
Ile Glu Cys Asp Asp Pro Val Ile Phe Leu Glu Pro Lys Arg Leu Tyr
            165                 170                 175

AAC GGC CCG TTC GAC GGC CAC CAT GAC CGC CCG GTT ACG CCG TGG TCG        2659
Asn Gly Pro Phe Asp Gly His His Asp Arg Pro Val Thr Pro Trp Ser
            180                 185                 190

AAA CAC CCG CAC AGC GCC GTG CCC GAT GGC TAC TAC ACC GTG CCA CTG        2707
Lys His Pro His Ser Ala Val Pro Asp Gly Tyr Tyr Thr Val Pro Leu
195                 200                 205                 210

GAC AAG GCC GCC ATC ACC CGC CCC GGC AAT GAC GTG AGC GTG CTC ACC        2755
Asp Lys Ala Ala Ile Thr Arg Pro Gly Asn Asp Val Ser Val Leu Thr
            215                 220                 225

TAT GGC ACC ACC GTG TAC GTG GCC CAG GTG GCC GCC GAA GAA AGT GGC        2803
Tyr Gly Thr Thr Val Tyr Val Ala Gln Val Ala Ala Glu Glu Ser Gly
            230                 235                 240

GTG GAT GCC GAA GTG ATC GAC CTG CGC AGC CTG TGG CCG CTA GAC CTG        2851
Val Asp Ala Glu Val Ile Asp Leu Arg Ser Leu Trp Pro Leu Asp Leu
            245                 250                 255

GAC ACC ATC GTC GAG TCG GTG AAA AAG ACC GGC CGT TGC GTG GTA GTA        2899
Asp Thr Ile Val Glu Ser Val Lys Lys Thr Gly Arg Cys Val Val Val
260                 265                 270

CAC GAG GCC ACC CGT ACT TGT GGC TTT GGC GCA GAA CTG GTG TCG CTG        2947
His Glu Ala Thr Arg Thr Cys Gly Phe Gly Ala Glu Leu Val Ser Leu
275                 280                 285                 290

GTG CAG GAG CAC TGC TTC CAC CAC CTG GAG GCG CCG ATC GAG CGC GTC        2995
Val Gln Glu His Cys Phe His His Leu Glu Ala Pro Ile Glu Arg Val
            295                 300                 305

ACC GGT TGG GAC ACC CCC TAC CCT CAC GCG CAG GAA TGG GCT TAC TTC        3043
Thr Gly Trp Asp Thr Pro Tyr Pro His Ala Gln Glu Trp Ala Tyr Phe
            310                 315                 320

CCA GGG CCT TCG CGG GTA GGT GCG GCA TTG AAA AAG GTC ATG GAG GTC        3091
Pro Gly Pro Ser Arg Val Gly Ala Ala Leu Lys Lys Val Met Glu Val
            325                 330                 335

TGAATG GGC ACG CAC GTC ATC AAG ATG CCG GAC ATT GGC GAA GGC ATC        3139
       Gly Thr His Val Ile Lys Met Pro Asp Ile Gly Glu Gly Ile
                       5                  10

GCG CAG GTC GAA TTG GTG GAA TGG TTC GTC AAG GTG GGC GAC ATC ATC        3187
Ala Gln Val Glu Leu Val Glu Trp Phe Val Lys Val Gly Asp Ile Ile
15                  20                  25                  30

GCC GAG GAC CAA GTG GTA GCC GAC GTC ATG ACC GAC AAG GCC ACC GTG        3235
Ala Glu Asp Gln Val Val Ala Asp Val Met Thr Asp Lys Ala Thr Val
            35                  40                  45

GAA ATC CCG TCG CCG GTC AGC GGC AAG GTG CTG GCC CTG GGT GGC CAG        3283
Glu Ile Pro Ser Pro Val Ser Gly Lys Val Leu Ala Leu Gly Gly Gln
            50                  55                  60

CCA GGT GAA GTG ATG GCG GTC GGC AGT GAG CTG ATC CGC ATC GAA GTG        3331
Pro Gly Glu Val Met Ala Val Gly Ser Glu Leu Ile Arg Ile Glu Val
            65                  70                  75

GAA GGC AGC GGC AAC CAT GTG GAT GTG CCG CAA GCC AAG CCG GCC GAA        3379
Glu Gly Ser Gly Asn His Val Asp Val Pro Gln Ala Lys Pro Ala Glu
            80                  85                  90

GTG CCT GCG GCA CCG GTA GCC GCT AAA CCT GAA CCA CAG AAA GAC GTT        3427
Val Pro Ala Ala Pro Val Ala Ala Lys Pro Glu Pro Gln Lys Asp Val
95                  100                 105                 110

AAA CCG GCG GCG TAC CAG GCG TCA GCC AGC CAC GAG GCA GCG CCC ATC        3475
```

```
                                                              -continued

Lys Pro Ala Ala Tyr Gln Ala Ser Ala Ser His Glu Ala Ala Pro Ile
            115                 120                 125

GTG CCG CGC CAG CCG GGC GAC AAG CCG CTG GCC TCG CCG GCG GTG CGC        3523
Val Pro Arg Gln Pro Gly Asp Lys Pro Leu Ala Ser Pro Ala Val Arg
            130                 135                 140

AAA CGC GCC CTC GAT GCC GGC ATC GAA TTG CGT TAT GTG CAC GGC AGC        3571
Lys Arg Ala Leu Asp Ala Gly Ile Glu Leu Arg Tyr Val His Gly Ser
            145                 150                 155

GGC CCG GCC GGG CGC ATC CTG CAC GAA GAC CTC GAC GCG TTC ATG AGC        3619
Gly Pro Ala Gly Arg Ile Leu His Glu Asp Leu Asp Ala Phe Met Ser
    160                 165                 170

AAA CCG CAA AGC GCT GCC GGG CAA ACC CCC AAT GGC TAT GCC AGG CGC        3667
Lys Pro Gln Ser Ala Ala Gly Gln Thr Pro Asn Gly Tyr Ala Arg Arg
175                 180                 185                 190

ACC GAC AGC GAG CAG GTG CCG GTG ATC GGC CTG CGC CGC AAG ATC GCC        3715
Thr Asp Ser Glu Gln Val Pro Val Ile Gly Leu Arg Arg Lys Ile Ala
                195                 200                 205

CAG CGC ATG CAG GAC GCC AAG CGC CGG GTC GCG CAC TTC AGC TAT GTG        3763
Gln Arg Met Gln Asp Ala Lys Arg Arg Val Ala His Phe Ser Tyr Val
            210                 215                 220

GAA GAA ATC GAC GTC ACC GCC CTG GAA GCC CTG CGC CAG CAG CTC AAC        3811
Glu Glu Ile Asp Val Thr Ala Leu Glu Ala Leu Arg Gln Gln Leu Asn
            225                 230                 235

AGC AAG CAC GGC GAC AGC CGC GGC AAG CTG ACA CTG CTG CCG TTC CTG        3859
Ser Lys His Gly Asp Ser Arg Gly Lys Leu Thr Leu Leu Pro Phe Leu
    240                 245                 250

GTG CGC GCC CTG GTC GTG GCA CTG CGT GAC TTC CCG CAG ATA AAC GCC        3907
Val Arg Ala Leu Val Val Ala Leu Arg Asp Phe Pro Gln Ile Asn Ala
255                 260                 265                 270

ACC TAC GAT GAC GAA GCG CAG ATC ATC ACC CGC CAT GGC GCG GTG CAT        3955
Thr Tyr Asp Asp Glu Ala Gln Ile Ile Thr Arg His Gly Ala Val His
                275                 280                 285

GTG GGC ATC GCC ACC CAA GGT GAC AAC GGC CTG ATG GTA CCC GTG CTG        4003
Val Gly Ile Ala Thr Gln Gly Asp Asn Gly Leu Met Val Pro Val Leu
            290                 295                 300

CGC CAC GCC GAA GCG GGC AGC CTG TGG GCC AAT GCC GGT GAG ATT TCA        4051
Arg His Ala Glu Ala Gly Ser Leu Trp Ala Asn Ala Gly Glu Ile Ser
            305                 310                 315

CGC CTG GCC AAC GCT GCG CGC AAC AAC AAG GCC AGC CGC GAA GAG CTG        4099
Arg Leu Ala Asn Ala Ala Arg Asn Asn Lys Ala Ser Arg Glu Glu Leu
    320                 325                 330

TCC GGT TCG ACC ATT ACC CTG ACC AGC CTC GGC GCC CTG GGC GGC ATC        4147
Ser Gly Ser Thr Ile Thr Leu Thr Ser Leu Gly Ala Leu Gly Gly Ile
335                 340                 345                 350

GTC AGC ACG CCG GTG GTC AAC ACC CCG GAA GTG GCG ATC GTC GGT GTC        4195
Val Ser Thr Pro Val Val Asn Thr Pro Glu Val Ala Ile Val Gly Val
                355                 360                 365

AAC CGC ATG GTT GAG CGG CCC GTG GTG ATC GAC GGC CAG ATC GTC GTG        4243
Asn Arg Met Val Glu Arg Pro Val Val Ile Asp Gly Gln Ile Val Val
            370                 375                 380

CGC AAG ATG ATG AAC CTG TCC AGC TCG TTC GAC CAC CGC GTG GTC GAT        4291
Arg Lys Met Met Asn Leu Ser Ser Ser Phe Asp His Arg Val Val Asp
            385                 390                 395

GGC ATG GAC GCC GCC CTG TTC ATC CAG GCC GTG CGT GGC CTG CTC GAA        4339
Gly Met Asp Ala Ala Leu Phe Ile Gln Ala Val Arg Gly Leu Leu Glu
    400                 405                 410

CAA CCC GCC TGC CTG TTC GTG GAG TGAGC ATG CAA CAG ACT ATC              4383
Gln Pro Ala Cys Leu Phe Val Glu       Met Gln Gln Thr Ile
415                 420                           5
```

```
CAG ACA ACC CTG TTG ATC ATC GGC GGC GGC CCT GGC GGC TAT GTG GCG      4431
Gln Thr Thr Leu Leu Ile Ile Gly Gly Gly Pro Gly Gly Tyr Val Ala
            10                  15                  20

GCC ATC CGC GCC GGG CAA CTG GGC ATC CCT ACC GTG CTG GTG GAA GGC      4479
Ala Ile Arg Ala Gly Gln Leu Gly Ile Pro Thr Val Leu Val Glu Gly
        25                  30                  35

CAG GCG CTG GGC GGT ACC TGC CTG AAC ATC GGC TGC ATT CCG TCC AAG      4527
Gln Ala Leu Gly Gly Thr Cys Leu Asn Ile Gly Cys Ile Pro Ser Lys
    40                  45                  50

GCG CTG ATC CAT GTG GCC GAG CAG TTC CAC CAG GCC TCG CGC TTT ACC      4575
Ala Leu Ile His Val Ala Glu Gln Phe His Gln Ala Ser Arg Phe Thr
55                  60                  65

GAA CCC TCG CCG CTG GGC ATC AGC GTG GCT TCG CCA CGC CTG GAC ATC      4623
Glu Pro Ser Pro Leu Gly Ile Ser Val Ala Ser Pro Arg Leu Asp Ile
70                  75                  80                  85

GGC CAG AGC GTG GCC TGG AAA GAC GGC ATC GTC GAT CGC CTG ACC ACT      4671
Gly Gln Ser Val Ala Trp Lys Asp Gly Ile Val Asp Arg Leu Thr Thr
                90                  95                  100

GGT GTC GCC GCC CTG CTG AAA AAG CAC GGG GTG AAG GTG GTG CAC GGC      4719
Gly Val Ala Ala Leu Leu Lys Lys His Gly Val Lys Val Val His Gly
            105                 110                 115

TGG GCC AAG GTG CTT GAT GGC AAG CAG GTC GAG GTG GAT GGC CAG CGC      4767
Trp Ala Lys Val Leu Asp Gly Lys Gln Val Glu Val Asp Gly Gln Arg
        110                 115                 120

ATC CAG TGC GAG CAC CTG TTG CTG GCC ACG GGC TCC AGC AGT GTC GAA      4815
Ile Gln Cys Glu His Leu Leu Leu Ala Thr Gly Ser Ser Ser Val Glu
    125                 130                 135

CTG CCG ATG CTG CCG TTG GGT GGG CCG GTG ATT TCC TCG ACC GAG GCC      4863
Leu Pro Met Leu Pro Leu Gly Gly Pro Val Ile Ser Ser Thr Glu Ala
140                 145                 150                 155

CTG GCA CCG AAA GCC CTG CCG CAA CAC CTG GTG GTG GTG GGC GGT GGC      4911
Leu Ala Pro Lys Ala Leu Pro Gln His Leu Val Val Val Gly Gly Gly
                160                 165                 170

TAC ATC GGC CTG GAG CTG GGT ATC GCC TAC CGC AAG CTC GGC GCG CAG      4959
Tyr Ile Gly Leu Glu Leu Gly Ile Ala Tyr Arg Lys Leu Gly Ala Gln
            175                 180                 185

GTC AGC GTG GTG GAA GCG CGC GAG CGC ATC CTG CCG ACT TAC GAC AGC      5007
Val Ser Val Val Glu Ala Arg Glu Arg Ile Leu Pro Thr Tyr Asp Ser
        190                 195                 200

GAA CTG ACC GCC CCG GTG GCC GAG TCG CTG AAA AAG CTG GGT ATC GCC      5055
Glu Leu Thr Ala Pro Val Ala Glu Ser Leu Lys Lys Leu Gly Ile Ala
    205                 210                 215

CTG CAC CTT GGC CAC AGC GTC GAA GGT TAC GAA AAT GGC TGC CTG CTG      5103
Leu His Leu Gly His Ser Val Glu Gly Tyr Glu Asn Gly Cys Leu Leu
220                 225                 230                 235

GCC AAC GAT GGC AAG GGC GGA CAA CTG CGC CTG GAA GCC GAC CGG GTG      5151
Ala Asn Asp Gly Lys Gly Gly Gln Leu Arg Leu Glu Ala Asp Arg Val
                240                 245                 250

CTG GTG GCC GTG GGC CGC CGC CCA CGC ACC AAG GGC TTC AAC CTG GAA      5199
Leu Val Ala Val Gly Arg Arg Pro Arg Thr Lys Gly Phe Asn Leu Glu
            255                 260                 265

TGC CTG GAC CTG AAG ATG AAT GGT GCC GCG ATT GCC ATC GAC GAG CGC      5247
Cys Leu Asp Leu Lys Met Asn Gly Ala Ala Ile Ala Ile Asp Glu Arg
        270                 275                 280

TGC CAG ACC AGC ATG CAC AAC GTC TGG GCC ATC GGC GAC GTG GCC GGC      5295
Cys Gln Thr Ser Met His Asn Val Trp Ala Ile Gly Asp Val Ala Gly
    285                 290                 295

GAA CCG ATG CTG GCG CAC CGG GCC ATG GCC CAG GGC GAG ATG GTG GCC      5343
Glu Pro Met Leu Ala His Arg Ala Met Ala Gln Gly Glu Met Val Ala
300                 305                 310                 315
```

```
GAG ATC ATC GCC GGC AAG GCA CGC CGC TTC GAA CCC GCT GCG ATA GCC          5391
Glu Ile Ile Ala Gly Lys Ala Arg Arg Phe Glu Pro Ala Ala Ile Ala
             320                 325                 330

GCC GTG TGC TTC ACC GAC CCG GAA GTG GTC GTG GTC GGC AAG ACG CCG          5439
Ala Val Cys Phe Thr Asp Pro Glu Val Val Val Val Gly Lys Thr Pro
             335                 340                 345

GAA CAG GCC AGT CAG CAA GGC CTG GAC TGC ATC GTC GCG CAG TTC CCG          5487
Glu Gln Ala Ser Gln Gln Gly Leu Asp Cys Ile Val Ala Gln Phe Pro
             350                 355                 360

TTC GCC GCC AAC GGC CGG GCC ATG AGC CTG GAG TCG AAA AGC GGT TTC          5535
Phe Ala Ala Asn Gly Arg Ala Met Ser Leu Glu Ser Lys Ser Gly Phe
             365                 370                 375

GTG CGC GTG GTC GCG CGG CGT GAC AAC CAC CTG ATC CTG GGC TGG CAA          5583
Val Arg Val Val Ala Arg Arg Asp Asn His Leu Ile Leu Gly Trp Gln
380              385                 390                 395

GCG GTT GGC GTG GCG GTT TCC GAG CTG TCC ACG GCG TTT GCC CAG TCG          5631
Ala Val Gly Val Ala Val Ser Glu Leu Ser Thr Ala Phe Ala Gln Ser
                 400                 405                 410

CTG GAG ATG GGT GCC TGC CTG GAG GAT GTG GCC GGT ACC ATC CAT GCC          5679
Leu Glu Met Gly Ala Cys Leu Glu Asp Val Ala Gly Thr Ile His Ala
             415                 420                 425

CAC CCG ACC CTG GGT GAA GCG GTA CAG GAA GCG GCA CTG CGT GCC CTG          5727
His Pro Thr Leu Gly Glu Ala Val Gln Glu Ala Ala Leu Arg Ala Leu
             430                 435                 440

GGC CAC GCC CTG CAT ATC TGACACTGAA GCGGCCGAGG CCGATTTGGC                 5775
Gly His Ala Leu His Ile
         445

CCGCCGCGCC GAGAGGCGCT GCGGGTCTTT TTTATACCTG TACCGGCAAA CCAATTCACT        5835

CGGCGATGGC ATTCTTGCNG GCCCTTTTGG CCCGGTACAT TGCCTTATCA GCCCNNNNCC        5895

AGNNGCGNAT GCTNGGTCCT CCCCTTCCTG CCACTGCACC ACGCCATAAC TCATGGTCAG        5955

ACGGCACTCC CCCACNGGTT NCAGTTNNCG CCATNCNNCC NNGNAAGCGC CCGGCGACAT        6015

CCAGCGCCTC GCCCAGCGTG CTCTGCGGCA GTACGATAAC GAACTCGTCC CGCCCCAGC        6075

GCGCCAACAG GTCCATGTTC GCGCAGGCAG GTCCGCAGGC TGTCGAC                     6122
```

(2) INFORMATION FOR SEQ ID NO:2:

(i) SEQUENCE CHARACTERISTICS:
  (A) LENGTH: 409 Amino acids
  (B) TYPE: Amino acid
  (D) TOPOLOGY: Linear (ii) MOLECULE TYPE: Protein (ix) FEATURE:
  (A) NAME/KEY: Alpha subunit of E1 component
  (B) LOCATION: 805-2031, Does not include initiating methionine
  (C) IDENTIFICATION METHOD: N-terminal amino acid sequence (x) PUBLICATION INFORMATION:
  (A) AUTHORS: Burns, Gayle
   Brown, Tracy
   Hatter, Kenneth
   Idriss, John. M.
   Sokatch, John R.
  (B) TITLE: Similarity of the E1 subunits of branched-chain
   oxoacid dehydrogenase from Pseudomonas putida to the
   corresponding subunits of mammalian branched-chain-
   oxoacid and pyruvate dehydrogenases
  (C) JOURNAL: European Journal of Biochemistry
  (D) VOLUME: 176
  (F) PAGES: 311-317
  (G) DATE: 1988

-continued (xi) SEQUENCE DESCRIPTION: SEQ ID NO:2:

Asn Glu Tyr Ala Pro Leu Arg Leu His Val Pro Glu Pro Thr Gly
              5                  10                  15

Arg Pro Gly Cys Gln Thr Asp Phe Ser Tyr Leu Arg Leu Asn Asp
             20                  25                  30

Ala Gly Gln Ala Arg Lys Pro Pro Val Asp Val Asp Ala Ala Asp
             35                  40                  45

Thr Ala Asp Leu Ser Tyr Ser Leu Val Arg Val Leu Asp Glu Gln
             50                  55                  60

Gly Asp Ala Gln Gly Pro Trp Ala Glu Asp Ile Asp Pro Gln Ile
             65                  70                  75

Leu Arg Gln Gly Met Arg Ala Met Leu Lys Thr Arg Ile Phe Asp
             80                  85                  90

Ser Arg Met Val Val Ala Gln Arg Gln Lys Lys Met Ser Phe Tyr
             95                 100                 105

Met Gln Ser Leu Gly Glu Glu Ala Ile Gly Ser Gly Gln Ala Leu
            110                 115                 120

Ala Leu Asn Arg Thr Asp Met Cys Phe Pro Thr Tyr Arg Gln Gln
            125                 130                 135

Ser Ile Leu Met Ala Arg Asp Val Ser Leu Val Glu Met Ile Cys
            140                 145                 150

Gln Leu Leu Ser Asn Glu Arg Asp Pro Leu Lys Gly Arg Gln Leu
            155                 160                 165

Pro Ile Met Tyr Ser Val Arg Glu Ala Gly Phe Phe Thr Ile Ser
            170                 175                 180

Gly Asn Leu Ala Thr Gln Phe Val Gln Ala Val Gly Trp Ala Met
            185                 190                 195

Ala Ser Ala Ile Lys Gly Asp Thr Lys Ile Ala Ser Ala Trp Ile
            200                 205                 210

Gly Asp Gly Ala Thr Ala Glu Ser Asp Phe His Thr Ala Leu Thr
            215                 220                 225

Phe Ala His Val Tyr Arg Ala Pro Val Ile Leu Asn Val Val Asn
            230                 235                 240

Asn Gln Trp Ala Ile Ser Thr Phe Gln Ala Ile Ala Gly Gly Glu
            245                 250                 255

Ser Thr Thr Phe Ala Gly Arg Gly Val Gly Cys Gly Ile Ala Ser
            260                 265                 270

Leu Arg Val Asp Gly Asn Asp Phe Val Ala Val Tyr Ala Ala Ser
            275                 280                 285

Arg Trp Ala Ala Glu Arg Ala Arg Arg Gly Leu Gly Pro Ser Leu
            290                 295                 300

Ile Glu Trp Val Thr Tyr Arg Ala Gly Pro His Ser Thr Ser Asp
            305                 310                 315

Asp Pro Ser Lys Tyr Arg Pro Ala Asp Trp Ser His Phe Pro
            320                 325                 330

Leu Gly Asp Pro Ile Ala Arg Leu Lys Gln His Leu Ile Lys Ile
            335                 340                 345

Gly His Trp Cys Glu Glu Glu His Gln Ala Thr Thr Ala Glu Phe
            350                 355                 360

Glu Ala Ala Val Ile Ala Ala Gln Lys Glu Ala Glu Gln Tyr Gly
            365                 370                 375

Thr Leu Ala Asn Gly His Ile Pro Ser Ala Ala Ser Met Phe Glu
            380                 385                 390

Asp Val Tyr Lys Glu Met Pro Asp His Leu Arg Arg Gln Arg Gln
              395                 400                 405

Glu Leu Gly Val (2) INFORMATION FOR SEQ ID NO:3:

(i) SEQUENCE CHARACTERISTICS:
      (A) LENGTH: 338 Amino acids
      (B) TYPE: Amino acid
      (D) TOPOLOGY: Linear (ii) MOLECULE TYPE: Protein (ix) FEATURE:
      (A) NAME/KEY: Beta subunit of E1 component
      (B) LOCATION: 2078-3091, Does not include inidiating
          methionine
      (C) IDENTIFICATION METHOD: N-terminal amino acid sequence (x) PUBLICATION INFORMATION:
      (A) AUTHORS: Burns, Gayle
          Brown, Tracy
          Hatter, Kenneth
          Idriss, John M.
          Sokatch, John R.
      (B) TITLE: Similarity of the E1 subunits of branched-chain-
          oxoacid dehydrogenase from Pseudomonas putida to the
          corresponding subunits of mammalian branched-chain-
          oxoacid and pyruvate dehydrogenases
      (C) JOURNAL: European Journal of Biochemistry
      (D) VOLUME: 176
      (F) PAGES: 31-317
      (G) DATE: 1988

(xi) SEQUENCE DESCRIPTION: SEQ ID NO:3:

Ala Thr Thr Thr Met Thr Met Ile Gln Ala Leu Arg Ser Ala Met
                5                  10                  15

Asp Val Met Leu Glu Arg Asp Asp Asn Val Val Val Tyr Gly Gln
               20                  25                  30

Asp Val Gly Tyr Phe Gly Gly Val Phe Arg Cys Thr Glu Gly Leu
               35                  40                  45

Gln Thr Lys Tyr Gly Lys Ser Arg Val Phe Asp Ala Pro Ile Ser
               50                  55                  60

Glu Ser Gly Ile Val Gly Thr Ala Val Gly Met Gly Ala Tyr Gly
               65                  70                  75

Leu Arg Pro Val Val Glu Ile Gln Phe Ala Asp Tyr Phe Tyr Pro
               80                  85                  90

Ala Ser Asp Gln Ile Val Ser Glu Met Ala Arg Leu Arg Tyr Arg
               95                 100                 105

Ser Ala Gly Glu Phe Ile Ala Pro Leu Thr Leu Arg Met Pro Cys
              110                 115                 120

Gly Gly Gly Ile Tyr Gly Gly Gln Thr His Ser Gln Ser Pro Glu
              125                 130                 135

Ala Met Phe Thr Gln Val Cys Gly Leu Arg Thr Val Met Pro Ser
              140                 145                 150

Asn Pro Tyr Asp Ala Lys Gly Leu Leu Ile Ala Ser Ile Glu Cys
              155                 160                 165

Asp Asp Pro Val Ile Phe Leu Glu Pro Lys Arg Leu Tyr Asn Gly
              170                 175                 180

Pro Phe Asp Gly His His Asp Arg Pro Val Thr Pro Trp Ser Lys
              185                 190                 195

His Pro His Ser Ala Val Pro Asp Gly Tyr Tyr Thr Val Pro Leu

```
                        200                 205                 210
Asp Lys Ala Ala Ile Thr Arg Pro Gly Asn Asp Val Ser Val Leu
                215                 220                 225
Thr Tyr Gly Thr Thr Val Tyr Val Ala Gln Val Ala Ala Glu Glu
                230                 235                 240
Ser Gly Val Asp Ala Glu Val Ile Asp Leu Arg Ser Leu Trp Pro
                245                 250                 255
Leu Asp Leu Asp Thr Ile Val Glu Ser Val Lys Lys Thr Gly Arg
                260                 265                 270
Cys Val Val Val His Glu Ala Thr Arg Thr Cys Gly Phe Gly Ala
                275                 280                 285
Glu Leu Val Ser Leu Val Gln Glu His Cys Phe His His Leu Glu
                290                 295                 300
Ala Pro Ile Glu Arg Val Thr Gly Trp Asp Thr Pro Tyr Pro His
                305                 310                 315
Ala Gln Glu Trp Ala Tyr Phe Pro Gly Pro Ser Arg Val Gly Ala
                320                 325                 330
Ala Leu Lys Lys Val Met Glu Val
                335
```

(2) INFORMATION FOR SEQ ID NO:4:

(i) SEQUENCE CHARACTERISTICS:
        (A) LENGTH: 422 Amino acids
        (B) TYPE: Amino acid
        (D) TOPOLOGY: Linear (ii) MOLECULE TYPE: Protein (ix) FEATURE:
        (A) NAME/KEY: E2 component
        (B) LOCATION: 3098-4363, does not include initiating
           methionine
        (C) IDENTIFICATION METHOD: N-terminal sequence (x) PUBLICATION INFORMATION:
        (A) AUTHORS: Burns, Gayle
           Brown, Tracy
           Hatter, Kenneth
           Sokatch, John R.
        (B) TITLE: Compaarison of the amion acid sequences of the
           transacylase components of branched-chain oxoacid
           dehydrogenase of Pseudomonas putida, and the pyruvate and
           2-oxoglutarate dehydrogenases of Escherichia coli
        (C) JOURNAL: European Journal of Biochemistry
        (D) VOLUME: 176
        (F) PAGES: 165-169
        (D) DATE: 1988

(xi) SEQUENCE DESCRIPTION: SEQ ID NO:4:

```
Gly Thr His Val Ile Lys Met Pro Asp Ile Gly Glu Gly Ile Ala
                5                   10                  15
Gln Val Glu Leu Val Glu Trp Phe Val Lys Val Gly Asp Ile Ile
                20                  25                  30
Ala Glu Asp Gln Val Val Ala Asp Val Met Thr Asp Lys Ala Thr
                35                  40                  45
Val Glu Ile Pro Ser Pro Val Ser Gly Lys Val Leu Ala Leu Gly
                50                  55                  60
Gly Gln Pro Gly Glu Val Met Ala Val Gly Ser Glu Leu Ile Arg
                65                  70                  75
Ile Glu Val Glu Gly Ser Gly Asn His Val Asp Val Pro Gln Ala
                80                  85                  90
```

-continued

```
Lys Pro Ala Glu Val Pro Ala Ala Pro Val Ala Ala Lys Pro Glu
             95                 100                 105

Pro Gln Lys Asp Val Lys Pro Ala Ala Tyr Gln Ala Ser Ala Ser
            110                 115                 120

His Glu Ala Ala Pro Ile Val Pro Arg Gln Pro Gly Asp Lys Pro
            125                 130                 135

Leu Ala Ser Pro Ala Val Arg Lys Arg Ala Leu Asp Ala Gly Ile
            140                 145                 150

Glu Leu Arg Tyr Val His Gly Ser Gly Pro Ala Gly Arg Ile Leu
            155                 160                 165

His Glu Asp Leu Asp Ala Phe Met Ser Lys Pro Gln Ser Ala Ala
            170                 175                 180

Gly Gln Thr Pro Asn Gly Tyr Ala Arg Arg Thr Asp Ser Glu Gln
            185                 190                 195

Val Pro Val Ile Gly Leu Arg Arg Lys Ile Ala Gln Arg Met Gln
            200                 205                 210

Asp Ala Lys Arg Arg Val Ala His Phe Ser Tyr Val Glu Glu Ile
            215                 220                 225

Asp Val Thr Ala Leu Glu Ala Leu Arg Gln Gln Leu Asn Ser Lys
            230                 235                 240

His Gly Asp Ser Arg Gly Lys Leu Thr Leu Leu Pro Phe Leu Val
            245                 250                 255

Arg Ala Leu Val Val Ala Leu Arg Asp Phe Pro Gln Ile Asn Ala
            260                 265                 270

Thr Tyr Asp Asp Glu Ala Gln Ile Ile Thr Arg His Gly Ala Val
            275                 280                 285

His Val Gly Ile Ala Thr Gln Gly Asp Asn Gly Leu Met Val Pro
            290                 295                 300

Val Leu Arg His Ala Glu Ala Gly Ser Leu Trp Ala Asn Ala Gly
            305                 310                 315

Glu Ile Ser Arg Leu Ala Asn Ala Ala Arg Asn Asn Lys Ala Ser
            320                 325                 330

Arg Glu Glu Leu Ser Gly Ser Thr Ile Thr Leu Thr Ser Leu Gly
            335                 340                 345

Ala Leu Gly Gly Ile Val Ser Thr Pro Val Val Asn Thr Pro Glu
            350                 355                 360

Val Ala Ile Val Gly Val Asn Arg Met Val Glu Arg Pro Val Val
            365                 370                 375

Ile Asp Gly Gln Ile Val Val Arg Lys Met Met Asn Leu Ser Ser
            380                 385                 390

Ser Phe Asp His Arg Val Val Asp Gly Met Asp Ala Ala Leu Phe
            395                 400                 405

Ile Gln Ala Val Arg Gly Leu Leu Glu Gln Pro Ala Cys Leu Phe
            410                 415                 420

Val Glu
```

(2) INFORMATION FOR SEQ ID NO:5:

(i) SEQUENCE CHARACTERISTICS:
        (A) LENGTH: 459 Amino acids
        (B) TYPE: Amino acid
        (D) TOPOLOGY: Linear (ii) MOLECULE TYPE: Protein (ix) FEATURE:

(A) NAME/KEY: Lpd-val, the E3 component
(B) LOCATION: 4369-5745, N-terminal methionine is present on mature protein
(C) IDENTIFICATION METHOD: Sequence of cyanogen bromide peptides (x) PUBLICATION INFORMATION:
(A) AUTHORS: Burns, Gayle
  Brown, Tracy
  Hatter, Kenneth
  Sokatch, John R.
(B) TITLE: Sequence analysis of the lpdV gene for lipoamide dehodrogenase of Pseudomonas putida
(C) JOURNAL: European Journal of Biochemistry
(D) VOLUME: 179
(F) PAGES: 61-69
(G) DATE: 1989

(xi) SEQUENCE DESCRIPTION: SEQ ID NO:5:

```
Met Gln Gln Thr Ile Gln Thr Thr Leu Leu Ile Ile Gly Gly Gly
                  5                  10                  15

Pro Gly Gly Tyr Val Ala Ala Ile Arg Ala Gly Gln Leu Gly Ile
                 20                  25                  30

Pro Thr Val Leu Val Glu Gly Gln Ala Leu Gly Gly Thr Cys Leu
                 35                  40                  45

Asn Ile Gly Cys Ile Pro Ser Lys Ala Leu Ile His Val Ala Glu
                 50                  55                  60

Gln Phe His Gln Ala Ser Arg Phe Thr Glu Pro Ser Pro Leu Gly
                 65                  70                  75

Ile Ser Val Ala Ser Pro Arg Leu Asp Ile Gly Gln Ser Val Ala
                 80                  85                  90

Trp Lys Asp Gly Ile Val Asp Arg Leu Thr Thr Gly Val Ala Ala
                 95                 100                 105

Leu Leu Lys Lys His Gly Val Lys Val Val His Gly Trp Ala Lys
                110                 115                 120

Val Leu Asp Gly Lys Gln Val Glu Val Asp Gly Gln Arg Ile Gln
                125                 130                 135

Cys Glu His Leu Leu Leu Ala Thr Gly Ser Ser Ser Val Glu Leu
                140                 145                 150

Pro Met Leu Pro Leu Gly Gly Pro Val Ile Ser Ser Thr Glu Ala
                155                 160                 165

Leu Ala Pro Lys Ala Leu Pro Gln His Leu Val Val Val Gly Gly
                170                 175                 180

Gly Tyr Ile Gly Leu Glu Leu Gly Ile Ala Tyr Arg Lys Leu Gly
                185                 190                 195

Ala Gln Val Ser Val Val Glu Ala Arg Glu Arg Ile Leu Pro Thr
                200                 205                 210

Tyr Asp Ser Glu Leu Thr Ala Pro Val Ala Glu Ser Leu Lys Lys
                215                 220                 225

Leu Gly Ile Ala Leu His Leu Gly His Ser Val Glu Gly Tyr Glu
                230                 235                 240

Asn Gly Cys Leu Leu Ala Asn Asp Gly Lys Gly Gly Gln Leu Arg
                245                 250                 255

Leu Glu Ala Asp Arg Val Leu Val Ala Val Gly Arg Arg Pro Arg
                260                 265                 270

Thr Lys Gly Phe Asn Leu Glu Cys Leu Asp Leu Lys Met Asn Gly
                275                 280                 285

Ala Ala Ile Ala Ile Asp Glu Arg Cys Gln Thr Ser Met His Asn
                290                 295                 300
```

Val Trp Ala Ile Gly Asp Val Ala Gly Glu Pro Met Leu Ala His
            305                 310                 315

Arg Ala Met Ala Gln Gly Glu Met Val Ala Glu Ile Ile Ala Gly
            320                 325                 330

Lys Ala Arg Arg Phe Glu Pro Ala Ala Ile Ala Ala Val Cys Phe
            335                 340                 345

Thr Asp Pro Glu Val Val Val Gly Lys Thr Pro Glu Gln Ala
            350                 355                 360

Ser Gln Gln Gly Leu Asp Cys Ile Val Ala Gln Phe Pro Phe Ala
            365                 370                 375

Ala Asn Gly Arg Ala Met Ser Leu Glu Ser Lys Ser Gly Phe Val
            380                 385                 390

Arg Val Val Ala Arg Arg Asp Asn His Leu Ile Leu Gly Trp Gln
            395                 400                 405

Ala Val Gly Val Ala Val Ser Glu Leu Ser Thr Ala Phe Ala Gln
            410                 415                 420

Ser Leu Glu Met Gly Ala Cys Leu Glu Asp Val Ala Gly Thr Ile
            425                 430                 435

His Ala His Pro Thr Leu Gly Glu Ala Val Gln Glu Ala Ala Leu
            440                 445                 450

Arg Ala Leu Gly His Ala Leu His Ile
            455

(2) INFORMATION FOR SEQ ID NO:6:

(i) SEQUENCE CHARACTERISTICS:
        (A) LENGTH: 792 Base pairs
        (B) TYPE: Nucleic acid
        (C) STRANDEDNESS: Double-stranded
        (D) TOPOLOGY: Circular (ii) MOLECULE TYPE: Nucleic acid (ix) FEATURE:
        (A) NAME/KEY: Control region regulating expression of the bkd
            operon
        (B) LOCATION: 1-792
        (C) IDENTIFICATION METHOD: S1 nuclease and reverse
            transcriptase mapping (x) PUBLICATION INFORMATION:
        (A) AUTHORS: Madhusudhan, K.T.
            Huang, G.
            Burns, Gayle
            Sokatch, John R.
        (B) TITLE: Transcriptional analysis of the promoter region of
            the branched chain keto acid dehyrogenase operon of
            Pseudomonas putida
        (C) JOURNAL: Journal of Bacteriology
        (D) VOLUME: 172
        (F) PAGES: 5655-5663
        (G) DATE: 1990

(xi) SEQUENCE DESCRIPTION: SEQ ID NO:6:

```
CGATGCCCTG GAGCTGAGCG ATGCTCATGA CGCTTGTCCT TGTTGTTGTA GGCTGACAAC      60

AACATAGGCT GGGGGTGTTT AAAATATCAA GCAGCCTCTC GAACGCCTGG GGCCTCTTCT     120

ATCGCGCAAG GTCATGCCAT TGGCCGGCAA CGGCAAGGCT GTCTTGTAGC GCACCTGTTT     180

CAAGGCAAAA CTCGAGCGGA TATTCGCCAC ACCCGGCAAC CGGGTCAGGT AATCGAGAAA     240

CCGCTCCAGC GCCTGGATAC TCGGCAGCAG TACCCGCAAC AGGTAGTCCG GGTCGCCCGT     300

CATCAGGTAG CACTCCATCA CCTCGGGCCG TTCGGCAATT TCTTCCTCGA AGCGGTGCAG     360
```

-continued

| | | | | |
|---|---|---|---|---|
| CGACTGCTCT | ACCTGTTTTT | CCAGGCTGAC | ATGGATGAAC | ACATTCACAT CCAGCCCCAA | 420 |
| CGCCTCGGGC | GACAACAAGG | TCACCTGCTG | GCGGATCACC | CCCAGTTCTT CCATGGCCCG | 480 |
| CACCCGGTTG | AAACAGGGCG | TGGGCGACAG | GTTGACCGAG | CGTGCCAGCT CGGCGTTGGT | 540 |
| GATGCGGGCG | TTTTCCTGCA | GGCTGTTGAG | AATGCCGATA | TCGGTACGAT CGAGTTTGCG | 600 |
| CATGAGACAA | AATCACCGGT | TTTTTGTGTT | TATGCGGAAT | GTTTATCTGC CCCGCTCGGC | 660 |
| AAAGGCAATC | AACTTGAGAG | AAAAATTCTC | CTGCCGGACC | ACTAAGATGT AGGGGACGCT | 720 |
| GACTTACCAG | TCACAAGCCG | GTACTCAGCG | GCGGCCGCTT | CAGAGCTCAC AAAAACAAAT | 780 |
| ACCCGAGCGA GC | | | | | 792 |

(2) INFORMATION FOR SEQ ID NO:7:

(i) SEQUENCE CHARACTERISTICS:
        (A) LENGTH: 15 Bases
        (B) TYPE: Nucleic acid
        (C) STRANDEDNESS: Single stranded
        (D) TOPOLOGY: Linear (ii) MOLECULE TYPE: Nucleic acid
        (A) DESCRIPTION: Seq ID No:7 is a synthetic nucleic acid used
            to determine the transcriptional start of the bkd operon.

(ix) FEATURE:
        (A) NAME/KEY: Synthetic nucleic acid used to determine the
            transcriptional start of the bkd operon by primer
            extension from the 3' end.
        (B) LOCATION: Complementary to bases 256-270 of Seq ID No:1

(x) PUBLICATION INFORMATION:
        (A) AUTHORS: Madhusudhan,K.T.
            Huang,G.
            Burns,G.
            Sokatch,John R.
        (B) TITLE: Transcriptional analysis of the promoter region of
            the branched chain keto acid dehydrogenase operon of
            Pseudomonas putida
        (C) JOURNAL: Journal of Bacteriology
        (D) VOLUME: 172
        (F) PAGES: 5655-5663
        (G) DATE: 1990

(xi) SEQUENCE DESCRIPTION: SEQ ID NO:7:

| | |
|---|---|
| CTGCTGCCGA GTATC | 15 |

What is claimed is:

1. A recombinant DNA molecule comprising a sequence comprising:
    a branched chain keto acid dehydrogenase complex promoter of *Pseudomonas putida*.

2. The recombinant DNA molecule of claim 1 wherein the sequence for the promoter comprises Sequence ID No. 6.

3. A plasmid comprising the DNA molecule of claim 1.

4. A transformant bacterial host comprising the plasmid of claim 3.

5. A recombinant DNA molecule comprising a sequence comprising the following elements in the 5' to 3' direction, said elements which are operably linked:
    a branched chain keto acid dehydrogenase complex promoter of *Pseudomonas putida*; and
    genes encoding all the subunits of branched chain keto acid dehydrogenase complex of *Pseudomonas putida*.

6. The recombinant DNA molecule of claim 5 wherein the sequence is Sequence ID No. 1.

7. The recombinant DNA molecule of claim 1 wherein the sequence for the promoter comprises Sequence ID No. 6.

8. The recombinant DNA molecule of claim 5 wherein the sequence for the all the subunits of branched chain keto acid dehydrogenase complex comprise Sequence ID Nos. 2, 3, 4, and 5.

9. The recombinant DNA molecule of claim 5 wherein the sequence comprises Sequence ID Nos. 6, 2, 3, 4, and 5.

10. A plasmid comprising the DNA molecule of claim 5.

11. A transformant bacterial host comprising the plasmid of claim 10.

* * * * *